United States Patent
Felt

(10) Patent No.: US 9,164,666 B2
(45) Date of Patent: *Oct. 20, 2015

(54) LAYERED BODY TEMPLATE BASED MEDICAL RECORDS

(71) Applicant: Verizon Patent and Licensing Inc., Basking Ridge, NJ (US)

(72) Inventor: Michelle Felt, Randolph, NJ (US)

(73) Assignee: VERIZON PATENT AND LICENSING INC., Basking Ridge, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/180,837

(22) Filed: Feb. 14, 2014

(65) Prior Publication Data

US 2014/0164970 A1  Jun. 12, 2014

Related U.S. Application Data

(63) Continuation of application No. 13/301,915, filed on Nov. 22, 2011, now Pat. No. 8,655,843.

(51) Int. Cl.
  G06F 17/30 (2006.01)
  G06F 3/0484 (2013.01)
  G06F 19/00 (2011.01)

(52) U.S. Cl.
  CPC ............ G06F 3/0484 (2013.01); G06F 19/322 (2013.01); G06F 19/3406 (2013.01); G06F 19/3418 (2013.01)

(58) Field of Classification Search
  CPC ....... G06F 8/34; H01L 24/00; H01L 2924/00; H01L 2224/3224; H01L 2224/33
  USPC ................. 707/636, 803, 805; 715/222, 751, 715/762–763, 778
  See application file for complete search history.

(56) References Cited

U.S. PATENT DOCUMENTS

| | | | |
|---|---|---|---|
| 5,098,426 A | 3/1992 | Sklar et al. | |
| 6,888,546 B1 * | 5/2005 | Kim | 345/424 |
| 6,983,420 B1 | 1/2006 | Itou et al. | |
| 7,000,179 B2 | 2/2006 | Yankovich et al. | |
| 7,783,096 B2 * | 8/2010 | Chen et al. | 382/128 |
| 7,804,982 B2 | 9/2010 | Howard et al. | |
| 8,316,237 B1 | 11/2012 | Felsher et al. | |
| 2002/0119433 A1 | 8/2002 | Callender | |
| 2002/0173778 A1 | 11/2002 | Knopp et al. | |
| 2002/0198516 A1 | 12/2002 | Knopp et al. | |
| 2003/0197716 A1 | 10/2003 | Krueger | |
| 2004/0059321 A1 | 3/2004 | Knopp et al. | |
| 2004/0088650 A1 | 5/2004 | Killen et al. | |
| 2004/0213437 A1 | 10/2004 | Howard et al. | |
| 2004/0215719 A1 | 10/2004 | Altshuler | |
| 2006/0004745 A1 | 1/2006 | Kuhn et al. | |
| 2006/0036619 A1 | 2/2006 | Fuerst et al. | |
| 2007/0196007 A1 * | 8/2007 | Chen et al. | 382/131 |
| 2008/0001968 A1 | 1/2008 | Krueger | |
| 2008/0091780 A1 | 4/2008 | Balan et al. | |
| 2008/0233549 A1 * | 9/2008 | Daniels | 434/267 |
| 2009/0024365 A1 | 1/2009 | Kropaczek et al. | |

(Continued)

*Primary Examiner* — Hanh Thai

(57) ABSTRACT

A device receives medical data associated with a user of the device, and creates a body template based on the received medical data, where the body template includes layers that are representations of a human body associated with the user. The device also displays the body template to the user, where the user is capable of manipulating one or more layers of the body template in order to review the medical data.

20 Claims, 28 Drawing Sheets

(56) References Cited

U.S. PATENT DOCUMENTS

| | | |
|---|---|---|
| 2009/0089154 A1 | 4/2009 | Dion |
| 2009/0287331 A1 | 11/2009 | Chakraborty et al. |
| 2010/0100364 A1 | 4/2010 | Kropaczek et al. |
| 2010/0131283 A1 | 5/2010 | Linthicum et al. |
| 2010/0131293 A1 | 5/2010 | Linthicum et al. |
| 2010/0131874 A1 | 5/2010 | Linthicum et al. |
| 2010/0138231 A1 | 6/2010 | Linthicum et al. |
| 2010/0153234 A1 | 6/2010 | Goodson et al. |
| 2010/0254382 A1 | 10/2010 | Steffen et al. |
| 2011/0004110 A1* | 1/2011 | Shusterman .................. 600/509 |
| 2011/0025883 A1 | 2/2011 | Shkurko et al. |
| 2011/0026836 A1 | 2/2011 | Ptucha et al. |
| 2011/0026839 A1 | 2/2011 | Bogart et al. |
| 2011/0029553 A1 | 2/2011 | Bogart et al. |
| 2011/0029562 A1 | 2/2011 | Whitby et al. |
| 2011/0029635 A1 | 2/2011 | Shkurko et al. |
| 2011/0029914 A1 | 2/2011 | Whitby et al. |
| 2011/0157226 A1 | 6/2011 | Ptucha et al. |
| 2011/0157227 A1 | 6/2011 | Ptucha et al. |
| 2011/0157228 A1 | 6/2011 | Ptucha et al. |
| 2011/0285748 A1 | 11/2011 | Slatter et al. |
| 2011/0313934 A1 | 12/2011 | Van Roy et al. |
| 2012/0173969 A1 | 7/2012 | Schmid et al. |
| 2012/0284642 A1* | 11/2012 | Sitrick et al. .................. 715/753 |
| 2012/0284644 A1* | 11/2012 | Sitrick et al. .................. 715/753 |
| 2012/0284645 A1* | 11/2012 | Sitrick et al. .................. 715/753 |
| 2012/0284646 A1* | 11/2012 | Sitrick et al. .................. 715/753 |

* cited by examiner

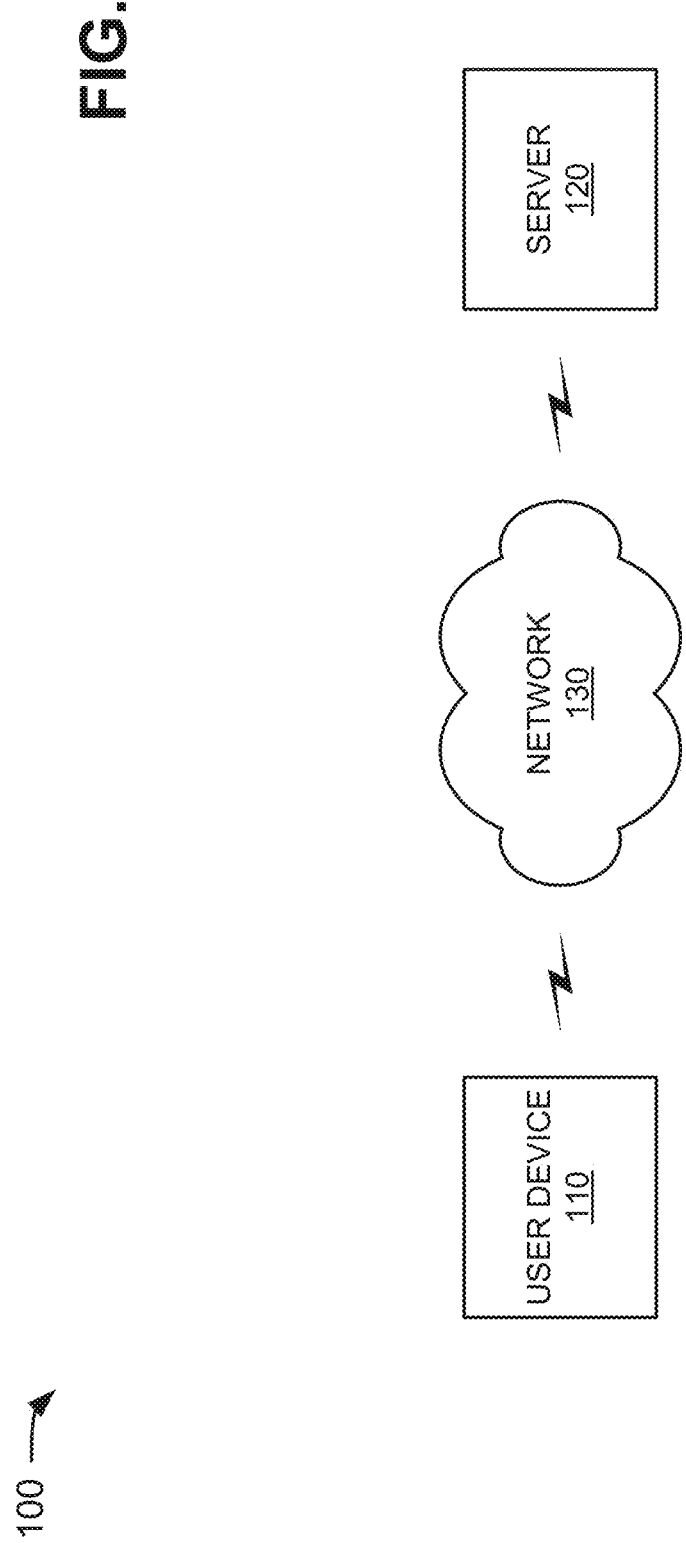

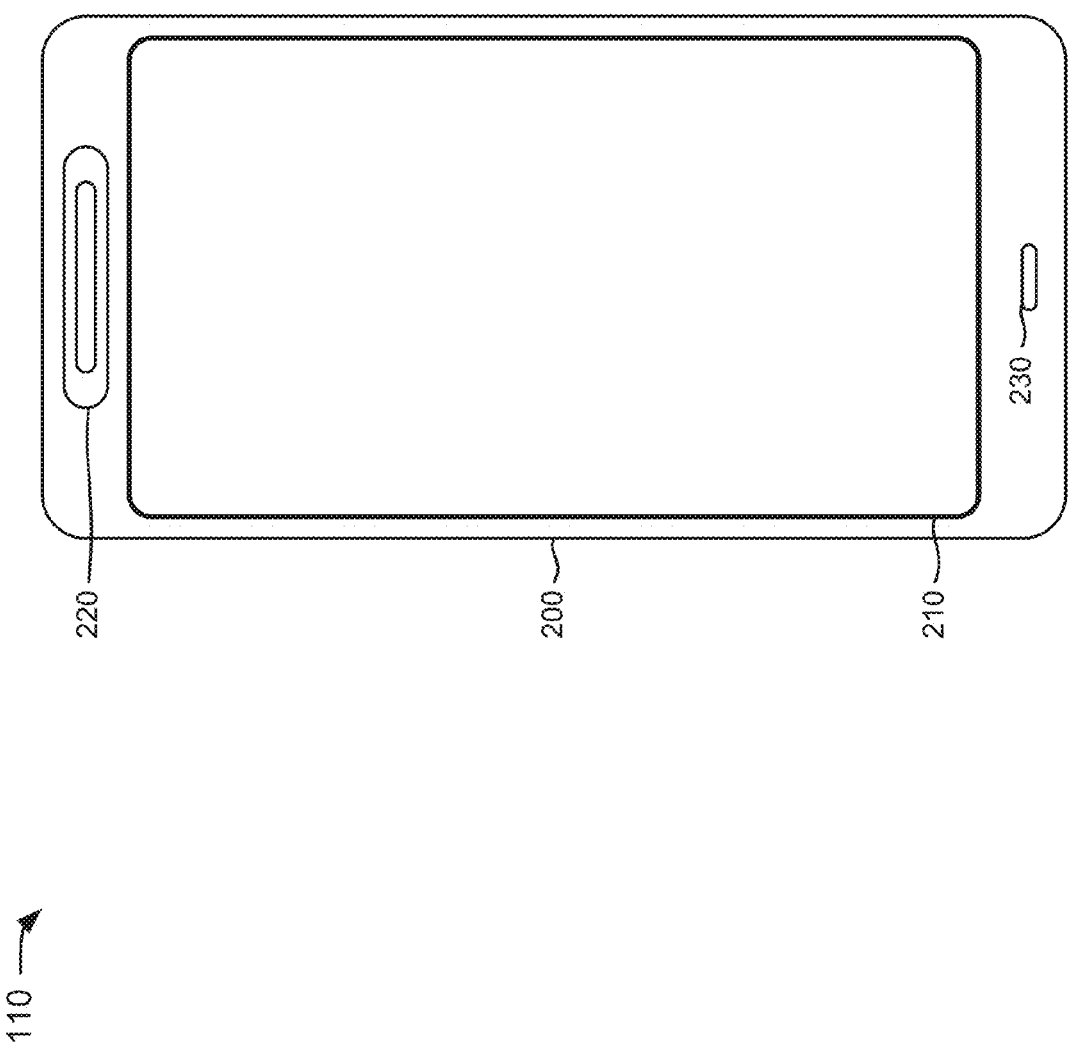

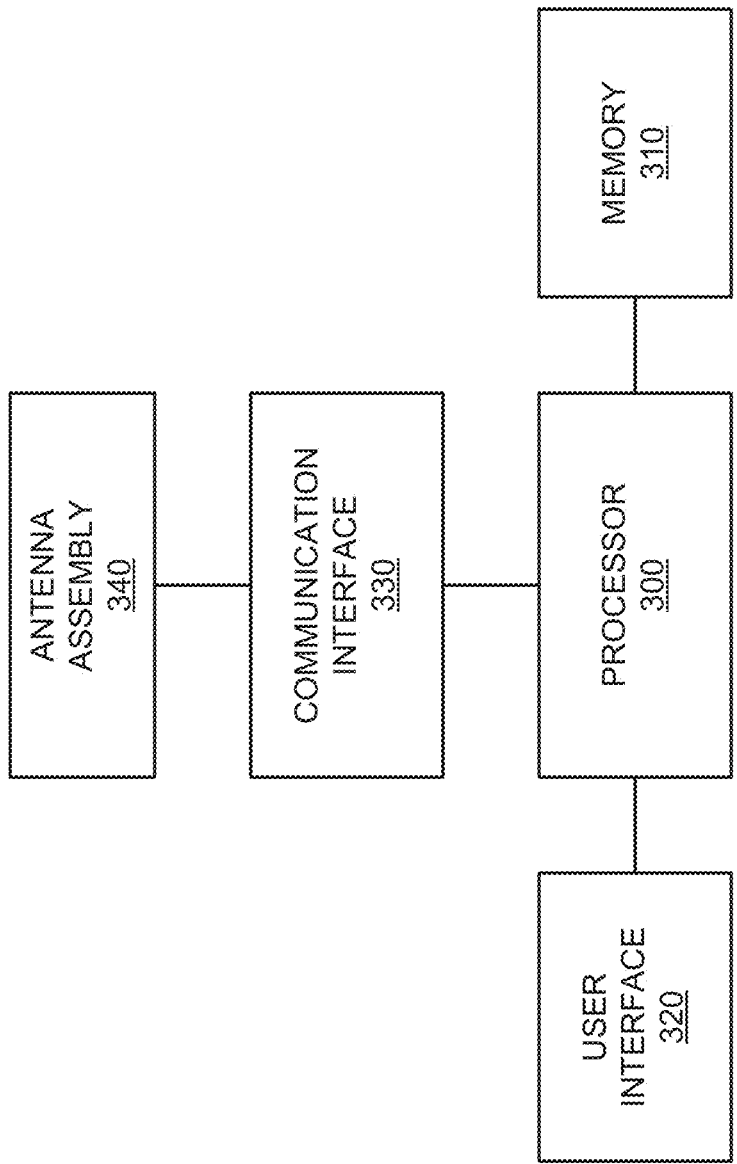

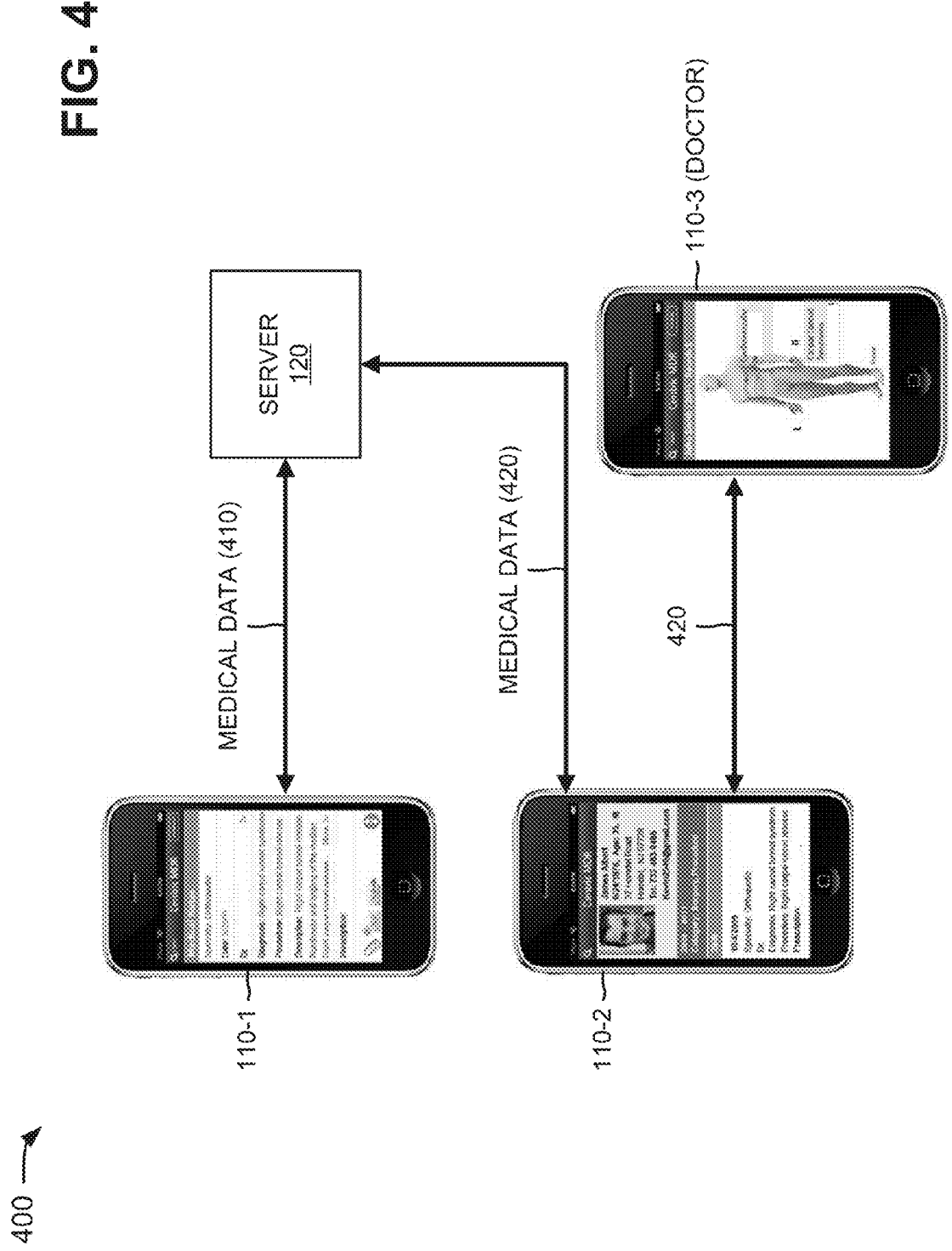

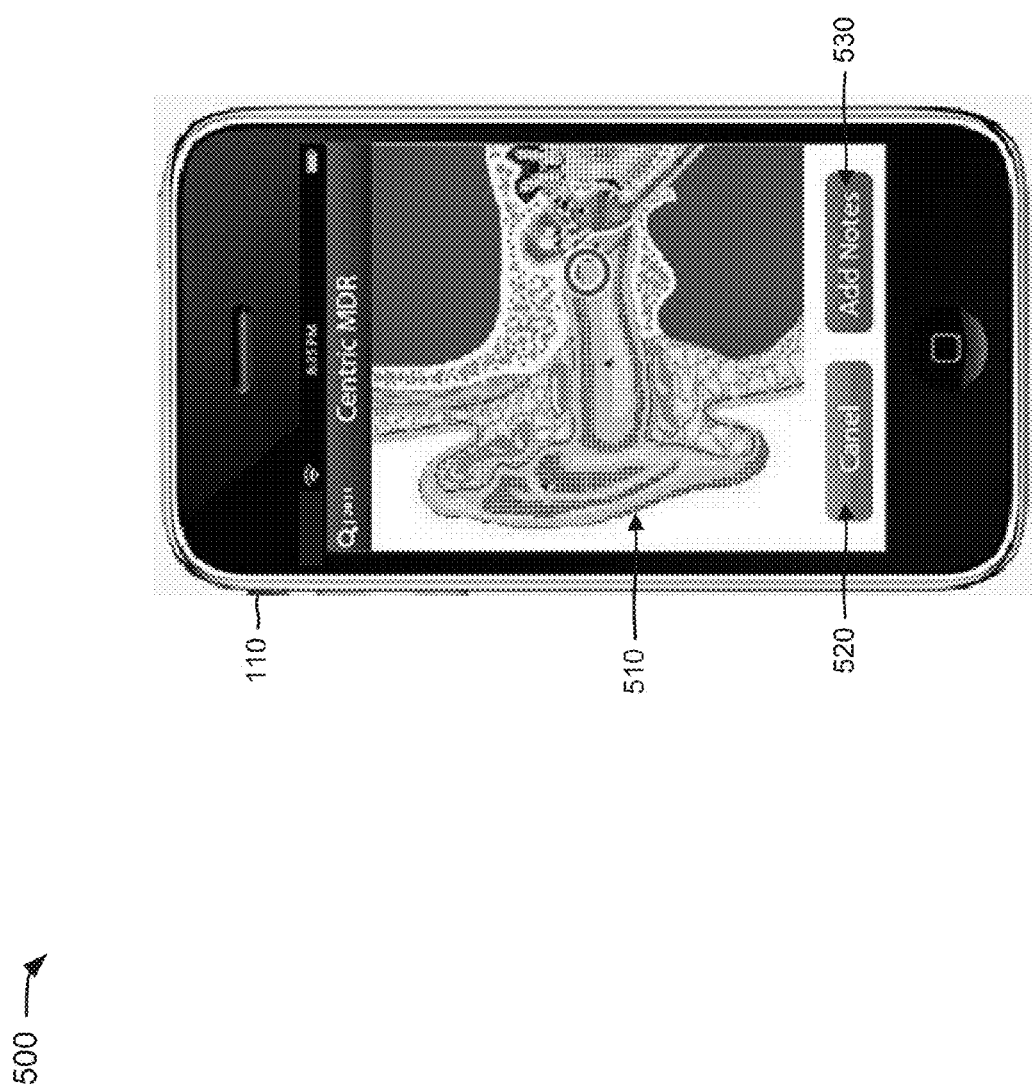

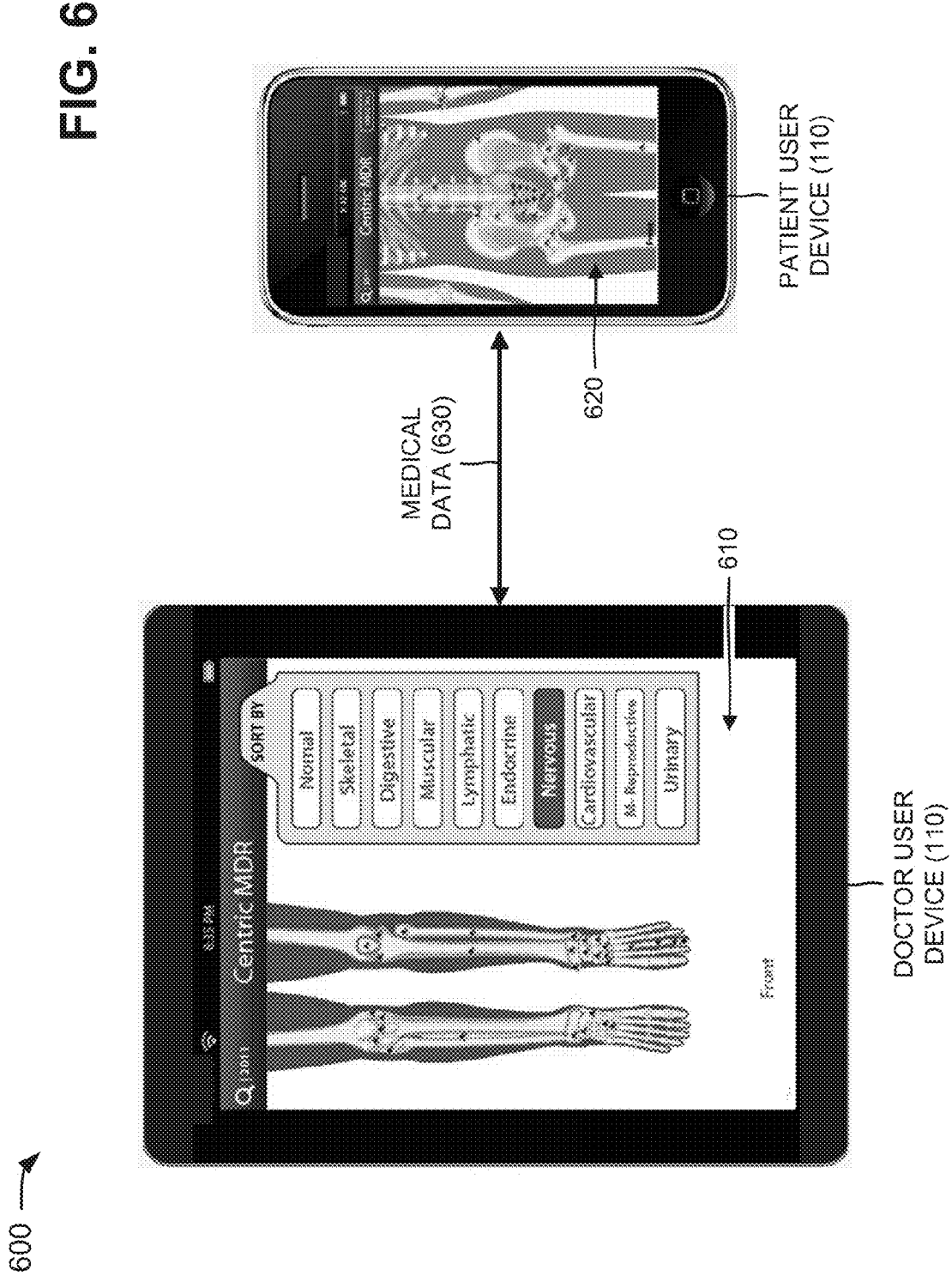

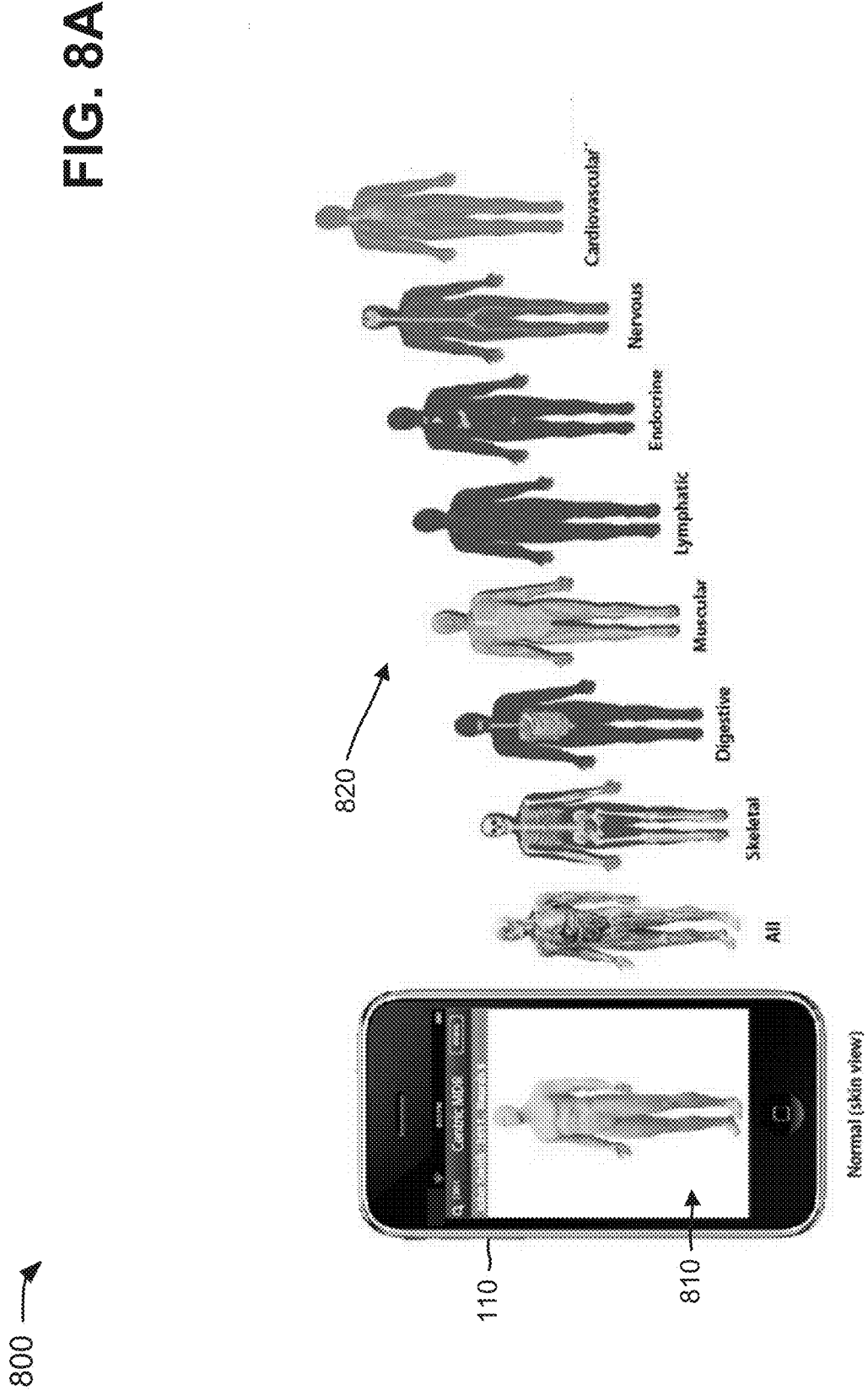

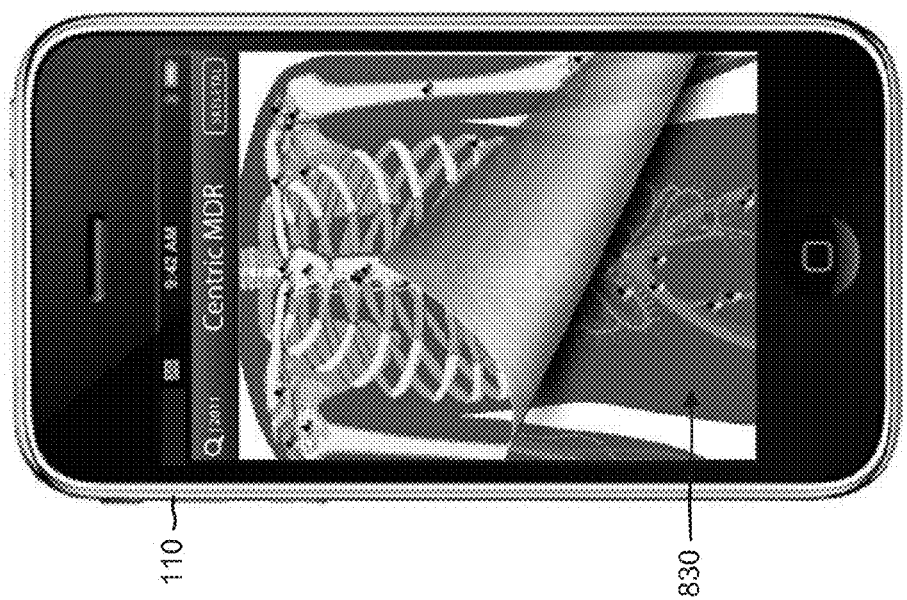

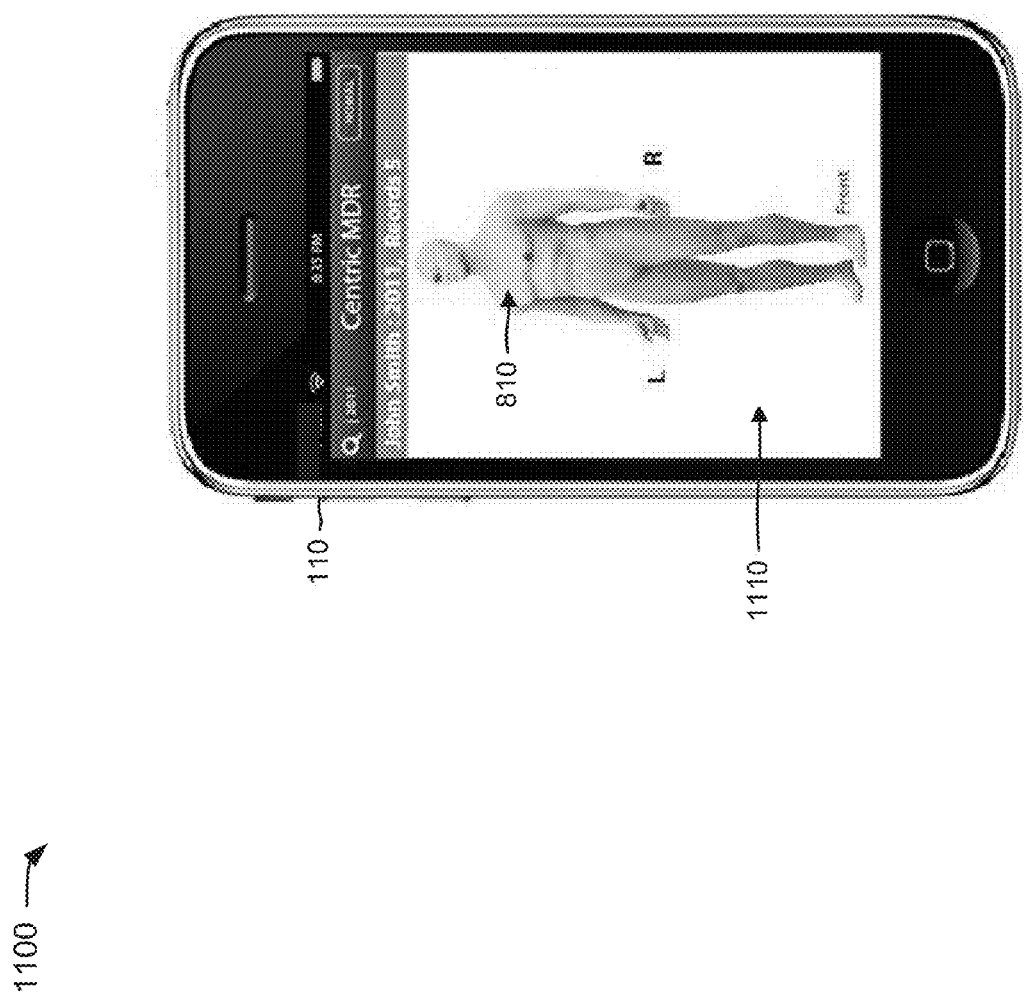

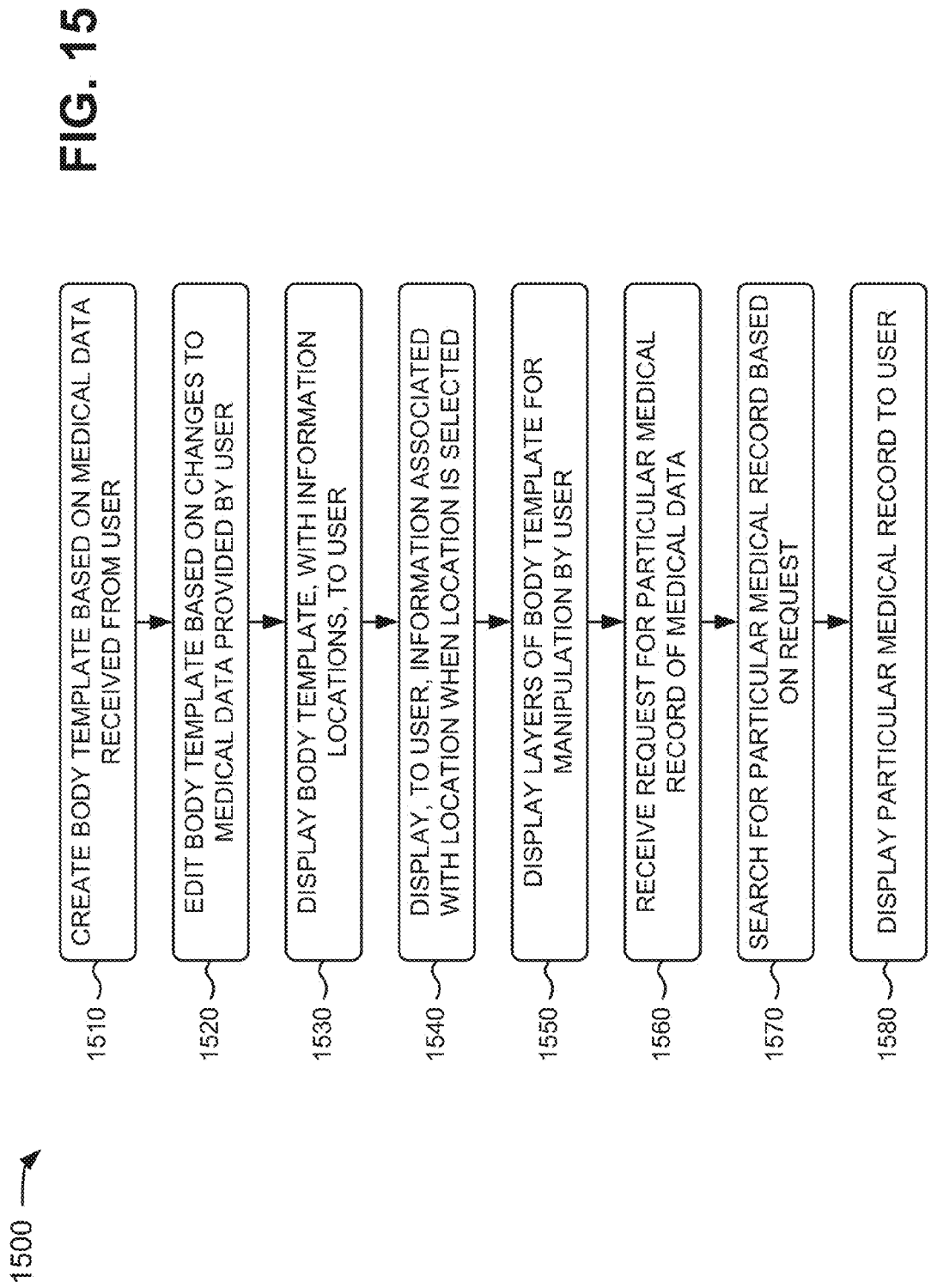

LAYERED BODY TEMPLATE BASED MEDICAL RECORDS

CROSS-REFERENCE TO RELATED APPLICATION

This application is a continuation of U.S. patent application Ser. No. 13/301,915 filed Nov. 22, 2011, the disclosure of which is hereby incorporated herein in its entirety.

BACKGROUND

Institutional upkeep of medical information, such as medical records or data, has been a problem area in many countries. Due to the sensitivity of patient medical data ownership and other controversial legal issues, patients are often unable to access any medical records at particular times, such as during doctor visits, during an emergency, etc. Therefore, storage and documentation of medical data by patients becomes even more necessary when patients consult multiple doctors and medical problems increase.

Obtaining and organizing medical records is very cumbersome and chaotic for doctors and patients. For example, a patient may visit different doctors, may have procedures performed by different doctors, and/or may take medications without informing the patient's family physician. In such scenarios, the family physician may find it very difficult to keep track of all the medical records of the patient. From the patient's perspective, collecting copies of doctor notes or lab test results from different doctors' offices is not easy. The patient has to file a medical release request form to obtain the medical records, and many doctors' offices are not willing to release any notes from the doctor. If the patient needs a second opinion from another doctor, it is difficult to access the previous doctor's notes or lab test results.

There is often a lack of communication between general physicians, specialist doctors, hospitals, labs, emergency rooms, etc., especially when they are not part of the same hospital or provider network. For example, some doctors record patient medical records into their systems, which are not accessible to other doctors. Even in countries with a government healthcare system, some of the patients' medical records may not be accessible if the patient visits doctors abroad or consults private doctors.

Furthermore, remembering medical data, such as complicated names of medications, is not easy for many patients. Particular procedures and/or names of diagnosed conditions are difficult to remember, especially for patients for whom English is a second language. Providing accurate medical information about family members, which may be important for diagnosing and treating genetically transmitted diseases, may also be difficult. In the end, not being able to provide correct medical information to a medical provider may lead to medical errors and may compromise patient safety.

BRIEF DESCRIPTION OF THE DRAWINGS

FIG. 1 is a diagram of an example network in which systems and/or methods described herein may be implemented;

FIG. 2 is a diagram of example external components of a user device of the network depicted in FIG. 1;

FIG. 3 is a diagram of example internal components of the user device of FIG. 2;

FIG. 4 is a diagram of example operations capable of being performed by an example portion of the network in FIG. 1;

FIGS. 5A and 5B are diagrams of example patient education user interfaces that may be generated or provided by the user device;

FIG. 6 is a diagram of example doctor and patient collaboration user interfaces that may be generated or provided by the user device;

FIGS. 8A and 8B are diagrams of example body template user interfaces that may be generated or provided by the user device;

FIGS. 11A and 11B are diagrams of example user interfaces, for reviewing medical records, which may be generated or provided by the user device;

FIGS. 15 and 16 are flow charts of an example process for providing layered body template-based medical records according to an implementation described herein.

DETAILED DESCRIPTION OF PREFERRED EMBODIMENTS

Figure 5B:
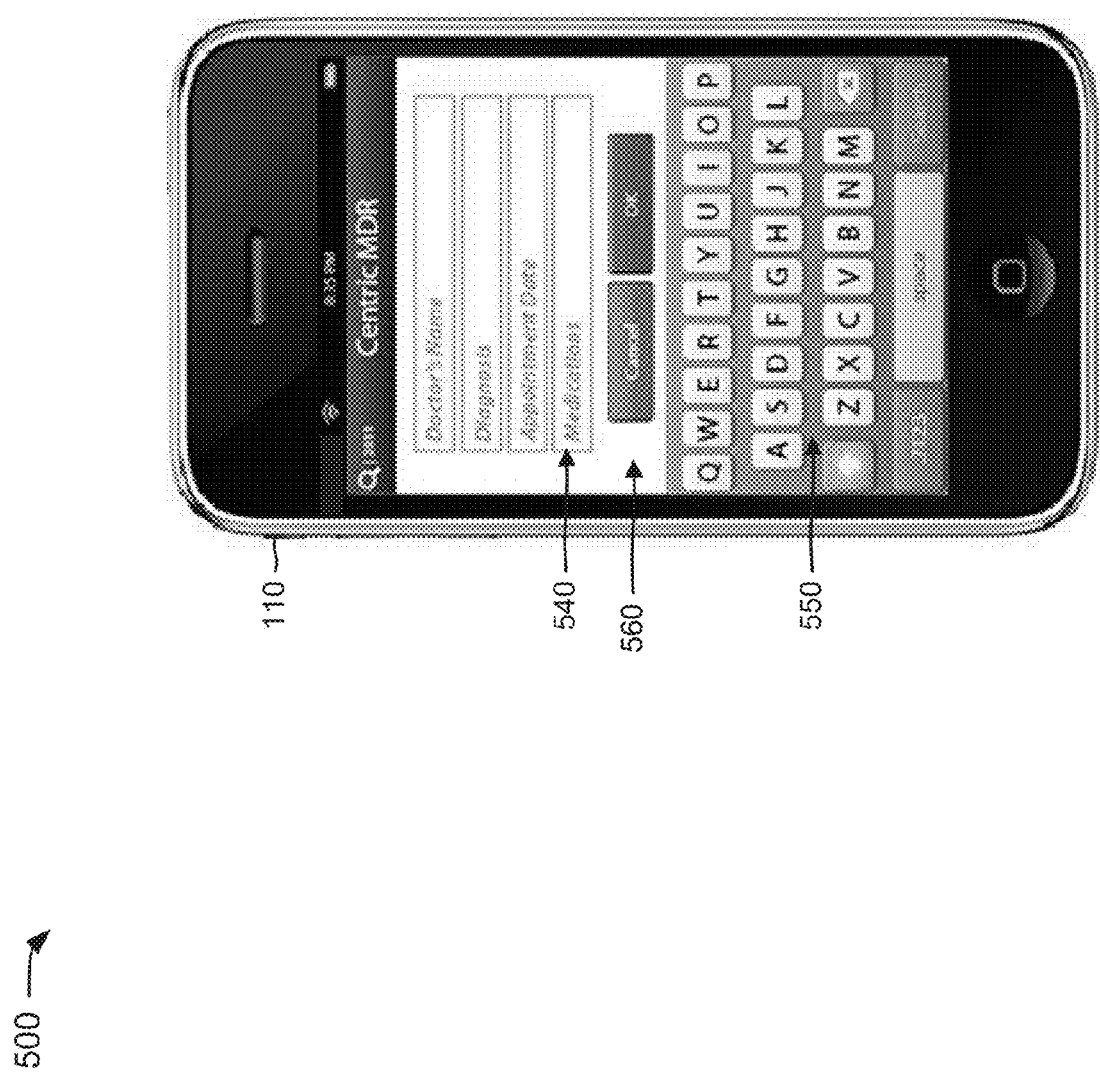

The following detailed description refers to the accompanying drawings. The same reference numbers in different drawings may identify the same or similar elements.

Systems and/or methods described herein may provide a centric medical record (MDR) application for storing patient medical information in a user device (e.g., a mobile computation and/or communication device) associated with a patient. The systems and/or methods may enhance the health and safety of the patient by reducing medical errors due to incorrect or unavailable medical information. The systems and/or methods may educate patients regarding their health, and may provide improved patient and doctor collaboration.

In one example implementation, a device, such as a mobile computation and/or communication device, may create a body template for a user of the device, based on medical data received from the user. The device may edit the body template based on changes to the medical data provided by the user, and may display the body template, with information locations, to the user. The device may display, to the user, information associated with a particular information location of the body template when the particular information location is selected by the user, and/or may display layers of the body template for manipulation by the user. The device may receive a request for a particular medical record of the medical data, may search for the particular medical record based on the request, and may display the particular medical record to the user.

As used herein, the terms "patient" and/or "user" may be used interchangeably. Also, the terms "patient" and/or "user" are intended to be broadly interpreted to include a user device or a user of a user device. Furthermore, the term "doctor" is intended to be broadly interpreted to include any type of medical provider or a user device associated with a medical provider.

The term "component," as used herein, is intended to be broadly construed to include hardware (e.g., a processor, a microprocessor, an application-specific integrated circuit (ASIC), a field-programmable gate array (FPGA), a chip, a memory device (e.g., a read only memory (ROM), a random access memory (RAM), etc.), etc.) or a combination of hardware and software (e.g., a processor, microprocessor, ASIC, etc. executing software contained in a memory device).

FIG. 1 is a diagram of an example network 100 in which systems and/or methods described herein may be implemented. As illustrated, network 100 may include a user device 110, a server 120, and a network 130. Devices and/or networks of network 100 may interconnect via wired and/or wireless connections. A single user device 110, server 120, and network 130 have been illustrated in FIG. 1 for simplicity. In practice, there may be more user devices 110, servers 120, and/or networks 130.

User device 110 may include a radiotelephone; a personal communications system (PCS) terminal that may combine, for example, a cellular radiotelephone with data processing and data communications capabilities; a smart phone; a personal digital assistant (PDA) that can include a radiotelephone, a pager, Internet/intranet access, etc.; a laptop computer; a tablet computer; a desktop computer; a workstation computer; or other types of computation and/or communication devices. In one example, user device 110 may include a mobile computation and/or communication device that is capable of communicating with server 120 via network 130.

Server 120 may include one or more server devices, or other types of computation or communication devices, that gather, process, search, and/or provide information in a manner described herein. In one example implementation, server 120 may include one or more devices that are capable of providing a centric MDR application to user device 110, via network 130. Server 120 may receive medical data, associated with a patient, from user device 110, and may store the medical data. Server 120 may receive a request for medical data from user device 110, may retrieve the requested medical data from storage, and may provide the requested medical data to user device 110.

Network 130 may include a local area network (LAN), a wide area network (WAN), a metropolitan area network (MAN), a telephone network, such as the Public Switched Telephone Network (PSTN), an intranet, the Internet, an optical fiber (or fiber optic)-based network, a cable television network, a satellite television network, or a combination of networks.

Although FIG. 1 shows example devices/networks of network 100, in other implementations, network 100 may include fewer devices/networks, different devices/networks, differently arranged devices/networks, or additional devices/networks than depicted in FIG. 1. Alternatively, or additionally, one or more devices/networks of network 100 may perform one or more other tasks described as being performed by one or more other devices/networks of network 100.

FIG. 2 is a diagram of example external components of user device 110. As shown, user device 110 may include a housing 200, a display 210, a speaker 220, and/or a microphone 230.

Housing 200 may protect the components of user device 110 from outside elements. Housing 200 may include a structure configured to hold devices and components used in user device 110, and may be formed from a variety of materials. For example, housing 200 may be formed from plastic, metal, a composite, etc., and may be configured to support display 210, speaker 220, and/or microphone 230.

Display 210 may provide visual information to the user. For example, display 210 may display text input into user device 110, text, images, video, and/or graphics received from another device, and/or information regarding incoming or outgoing calls or text messages, emails, media, games, phone books, address books, the current time, etc. In one implementation, display 210 may include a touch screen display that may be configured to receive a user input when the user touches display 210. For example, the user may provide an input to display 210 directly, such as via the user's finger, or via other input objects, such as a stylus. User inputs received via display 210 may be processed by components and/or devices operating in user device 110. The touch screen display may permit the user to interact with user device 110 in order to cause user device 110 to perform one or more operations.

Speaker 220 may provide audible information to a user of user device 110. Speaker 220 may be located in an upper portion of user device 110, and may function as an ear piece when a user is engaged in a communication session using user device 110. Speaker 220 may also function as an output device for music and/or audio information associated with games and/or video images played on user device 110.

Microphone 230 may receive audible information from the user. Microphone 230 may include a device that converts speech or other acoustic signals into electrical signals for use by user device 110. Microphone 230 may be located proximate to a lower side of user device 110.

Although FIG. 2 shows example components of user device 110, in other implementations, user device 110 may contain fewer components, different components, differently arranged components, or additional components than depicted in FIG. 2. Alternatively, or additionally, one or more components of user device 110 may perform one or more other tasks described as being performed by one or more other components of user device 110.

FIG. 3 is an example diagram of internal components of user device 110. As illustrated, user device 110 may include a processor 300, memory 310, a user interface 320, a communication interface 330, and/or an antenna assembly 340.

Processor 300 may include one or more processors or microprocessors that interpret and execute instructions. In other implementations, processor 300 may be implemented as or include one or more ASICs, FPGAs, or the like.

Memory 310 may include a RAM or another type of dynamic storage device that stores information and instructions for execution by processor 300, a ROM or another type of static storage device that stores static information and instructions for processor 300, and/or some other type of magnetic or optical recording medium and its corresponding drive for storing information and/or instructions.

User interface 320 may include mechanisms for inputting information to user device 110 and/or for outputting information from user device 110. Examples of input and output mechanisms might include buttons (e.g., control buttons, keys of a keypad, a joystick, etc.) or a touch screen interface (e.g., display 210) to permit data and control commands to be input into user device 110; a speaker (e.g., speaker 220) to receive electrical signals and output audio signals; a microphone (e.g., microphone 230) to receive audio signals and output electrical signals; a display (e.g., display 210) to output visual information (e.g., text input into user device 110); a vibrator to cause user device 110 to vibrate; etc.

Communication interface 330 may include, for example, a transmitter that may convert baseband signals from processor 300 to radio frequency (RF) signals and/or a receiver that may convert RF signals to baseband signals. Alternatively, communication interface 330 may include a transceiver to perform functions of both a transmitter and a receiver. Communication interface 330 may connect to antenna assembly 340 for transmission and/or reception of the RF signals.

Antenna assembly 340 may include one or more antennas to transmit and/or receive RF signals over the air. Antenna assembly 340 may, for example, receive RF signals from communication interface 330 and transmit them over the air, and receive RF signals over the air and provide them to communication interface 330. In one implementation, for example, communication interface 330 may communicate with a network and/or devices connected to a network.

As described herein, user device 110 may perform certain operations in response to processor 300 executing software instructions contained in a computer-readable medium, such as memory 310. A computer-readable medium may be defined as a non-transitory memory device. A memory device may include space within a single physical memory device or spread across multiple physical memory devices. The software instructions may be read into memory 310 from another computer-readable medium, or from another device via communication interface 330. The software instructions contained in memory 310 may cause processor 300 to perform processes described herein. Alternatively, hardwired circuitry may be used in place of or in combination with software instructions to implement processes described herein. Thus, implementations described herein are not limited to any specific combination of hardware circuitry and software.

Although FIG. 3 shows example components of user device 110, in other implementations, user device 110 may contain fewer components, different components, differently arranged components, or additional components than depicted in FIG. 3. Alternatively, or additionally, one or more components of user device 110 may perform one or more other tasks described as being performed by one or more other components of user device 110.

FIG. 4 is a diagram of example operations capable of being performed by an example portion 400 of network 100 (FIG. 1). As shown, network portion 400 may include three user devices 110-1, 110-2, and 110-3, and server 120. User devices 110 and server 120 may include the features described above in connection with, for example, one or more of FIGS. 1-3. User device 110-1 may be associated with a first user or patient (not shown). User device 110-2 may be associated with a second user or patient (not shown). User device 110-3 may be associated with a doctor (not shown) of the second user.

Although not shown in FIG. 4, user devices 110 may download a centric MDR application from server 120, and the centric MDR application may be installed on user devices 110. In one example, the centric MDR application may include a mobile application that enables a user to input and store patient medical information in user devices 110. For example, the centric MDR application may enable the first user to input and store medical data 410 in user device 110-1 (e.g., in memory 310). Medical data 410 may include an age, a height, a weight, and/or other physical characteristics of the first user or a family member of the first user; whether the first user/family member smokes; whether the first user/family member drinks alcohol; prescriptions or medications taken by the first user/family member; medical conditions of the first user/family member; surgeries received by the first user/family member; diseases of the first user/family member; etc.

Alternative, or additionally, the centric MDR application may enable the second user to input and store medical data 420 in user device 110-2 (e.g., in memory 310). Medical data 420 may include an age, a height, a weight, and/or other physical characteristics of the second user or a family member of the second user; whether the second user/family member smokes; whether the second user/family member drinks alcohol; prescriptions or medications taken by the second user/family member; medical conditions of the second user/family member; surgeries received by the second user/family member; diseases of the second user/family member; etc. Alternatively, or additionally, the centric MDR application may enable the doctor to use, for example, user device 110-3 to input and store medical data associated with various patients, such as medical data 410 associated with the first user and medical data 420 associated with the second user. Medical data 410 and/or 420 may also include images of medical documents, X-rays, insurance forms, etc. associated with the first user, the second user, and/or family members of the first user and/or the second user.

As further shown in FIG. 4, the first user may instruct user device 110-1 to provide medical data 410 to server 120. Server 120 may receive medical data 410 and may store medical data 410 in a memory device associated with server 120. The first user may also instruct user device 110-1 to retrieve medical data 410 from server 120. The second user may instruct user device 110-2 to provide medical data 420 to server 120. Server 120 may receive medical data 420 and may store medical data 420 in the memory device associated with server 120. The second user may also instruct user device 110-2 to retrieve medical data 420 from server 120. The doctor may instruct user device 110-3 to provide medical data 410 and/or medical data 420 to server 120 (not shown in FIG. 4).

The centric MDR application may enable patients to document and store individual medical records by enabling each patient to keep track of his or her family's medical data. The medical data may be collected and added to the centric MDR application by the patient and doctor collaborating with each other. The medical data may be stored in a cloud computing environment (e.g., server 120), and may be referenced, downloaded, and/or updated via a mobile user device 110 (e.g., a smart phone, a PDA, a tablet computer, etc.) and/or a fixed user device 110 (e.g., a desktop computer, a workstation computer, etc.). If a doctor and a patient both utilize the centric MDR application, the doctor and the patient may more easily exchange medical data since a format of the medical data may be the same or similar. For example, as shown in FIG. 4, the second user may instruct user device 110-2 to provide medical data 420 to user device 110-3 of the doctor. Alternatively, or additionally, the doctor may instruct user device 110-3 to provide medical data 420 to user device 110-2 of the second user.

In one example implementation, the centric MDR application may enable user devices 110-2 and 110-3 to connect via short-range wireless communication protocols for a wireless personal area network (WPAN) and/or a wireless local area network (WLAN), such as, for example, IEEE 802.15 (e.g., Bluetooth) and IEEE 802.11 (e.g., Wi-Fi). Once user devices 110-2 and 110-3 are connected, the doctor may perform a flicking finger gesture on a display of user device 110-3 by sliding a finger across the display of user device 110-3 in a direction of user device 110-2. The flicking finger gesture may instruct user device 110-3 to transfer medical data 420 to user device 110-2. Alternatively, or additionally, the second user may utilize a similar flicking finger gesture to instruct user device 110-2 to transfer medical data 420 to user device 110-3. In one example, the doctor may limit what information, from medical data 420, is provided to the second user, and/or the second user may limit what information, from medical data 420, is provided to the doctor.

Although FIG. 4 shows example components of network portion 400, in other implementations, network portion 400 may include fewer components, different components, differently arranged components, or additional components than depicted in FIG. 4. Additionally, or alternatively, one or more components of network portion 400 may perform one or more other tasks described as being performed by one or more other components of network portion 400.

FIGS. 5A and 5B are diagrams of example patient education user interfaces 500 that may be generated or provided by user device 110. User interfaces 500 depicted in FIGS. 5A and 5B, as well as the user interfaces depicted in FIGS. 6-14C (hereinafter referred to collectively as "the user interfaces") may include graphical user interfaces (GUIs) or non-graphical user interfaces, such as text-based interfaces. The user interfaces may provide information to users via customized interfaces (e.g., proprietary interfaces) and/or other types of interfaces (e.g., browser-based interfaces, etc.). The user interfaces may receive user inputs via one or more input devices (e.g., display 210, FIG. 2), may be user-configurable (e.g., a user may change the size of the user interfaces, information displayed in the user interfaces, color schemes used by the user interfaces, positions of text, images, icons, windows, etc., in the user interfaces, etc.), and/or may not be user-configurable. Information associated with the user interfaces may be selected and/or manipulated by a user of user device 110 (e.g., via a touch screen display, a mouse, a keyboard, a keypad, voice commands, etc.).

A patient may become more aware of his or her health and gain knowledge by providing new information to the centric MDR application. By viewing user interfaces of the centric MDR application, the patient may more easily understand what doctors are saying. Thus, the centric MDR application may motivate the patient to become more responsible for his or her health and to check his or her health more regularly.

For example, as shown in FIG. 5A, if a daughter is diagnosed with an ear infection, a mother may enter information associated with the ear infection into user device 110, and the centric MDR application may display an image 510 of the daughter's ear infection based on the entered information. Alternatively, or additionally, the daughter's doctor may provide (e.g., via another user device 110) the information associated with the ear infection to the mother's user device 110. The centric MDR application may enable the mother to cancel the display of image 510 by user device 110, as indicated by reference number 520, and may enable the mother to enter notes associated with the ear infection, as indicated by reference number 530. Alternatively, or additionally, the daughter's doctor may provide (e.g., via another user device 110) the ear infection notes to the mother's user device 110.

As shown in FIG. 5B, the centric MDR application may enable a user to input a variety of medical information 540 to user device 110 via a virtual keypad 550 displayed by user device 110. Alternatively, or additionally, medical information 540 may be provided to user device 110 via a keypad, a keyboard, voice commands, and/or other input mechanisms. Medical information 540 may include a doctor's name, a diagnosis received from the doctor, an appointment date, medications prescribed by the doctor, etc. In one example implementation, medications received by the centric MDR application may be automatically linked to a pharmacy database (e.g., associated with a pharmacy) so that orders for the medications may be automatically placed. Once the user has entered medical information 540, the user may submit medical information 540 for storage in user device 110 by selecting a selection mechanism 560 (e.g., an "OK" icon, link, button, etc.).

FIG. 6 is a diagram of example doctor and patient collaboration user interfaces 600 that may be generated or provided by user device 110. As shown, the centric MDR application may enable a doctor's user device 110 to display medical data of a patient, as indicated by reference number 610. Medical data 610 may include, for example, a front view of the patient's lower skeletal system. The centric MDR application may also enable the patient's user device 110 to display the same or different medical data of the patient, as indicated by reference number 620. Medical data 620 may include, for example, a front view of the patient's middle skeletal system.

As further shown in FIG. 6, the centric MDR application may enable the doctor's user device 110 and the patient's user device 110 to exchange medical data 630. Medical data 630 may include an age, a height, a weight, and/or other physical characteristics of the patient or a family member of the patient; whether the patient/family member smokes; whether the patient/family member drinks alcohol; prescriptions or medications taken by the patient/family member; medical conditions of the patient/family member; surgeries received by the patient/family member; diseases of the patient/family member; etc.

At the doctor's office, the centric MDR application may facilitate doctor and patient collaboration. For example, the centric MDR application may enable the doctor to show an area of the patient's inner body using the doctor's user device 110 and/or the patient's user device 110, instead of drawing body parts on pieces of paper or showing a picture from medical charts or an X-ray.

The centric MDR application may be used to provide motivation to patients. For example, in the case of a growing child, the child's growth may be viewed graphically by converting the child's height and weight, which may be periodically provided to the centric MDR application, into proportionate figures. In another example, an adult's weight change may be viewed graphically by converting the adult's weight, which may be periodically provided to the centric MDR application, into proportionate figures. Such graphic representations may provide a clearer idea about changes occurring in a user's body.

Figure 7A:
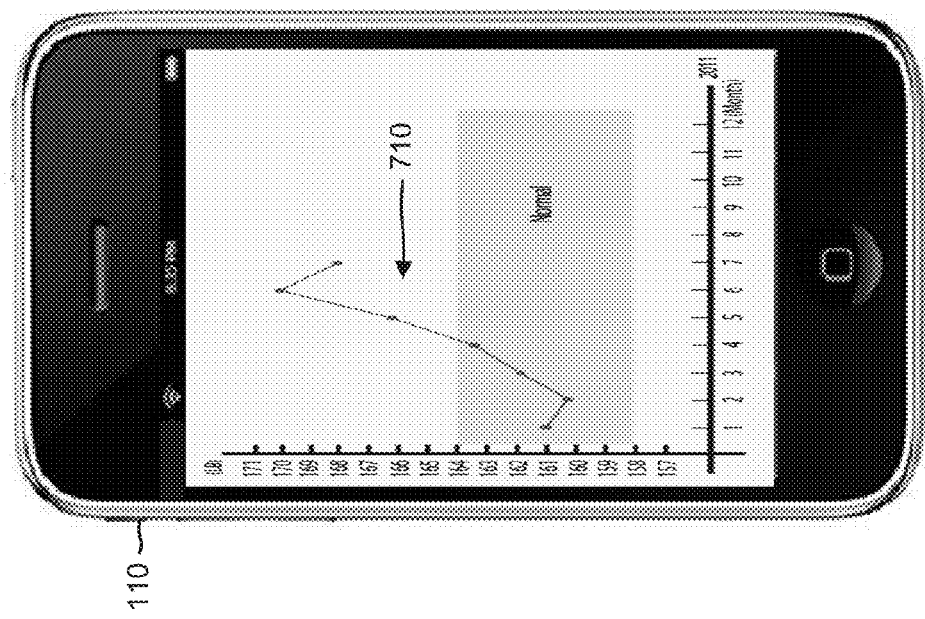
FIGS. 7A-7C are diagrams of example patient motivation user interfaces that may be generated or provided by the user device.
Figure 7B:
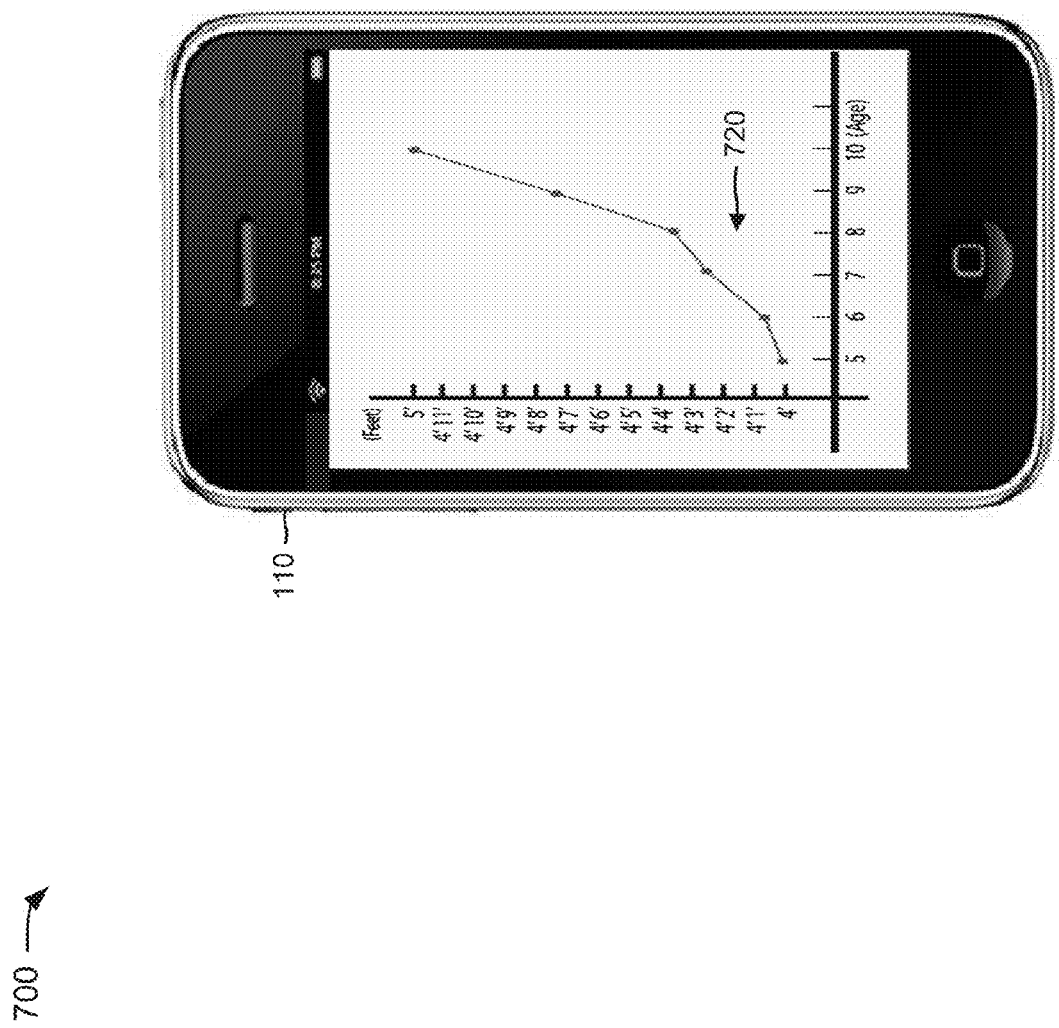
Figure 7C:
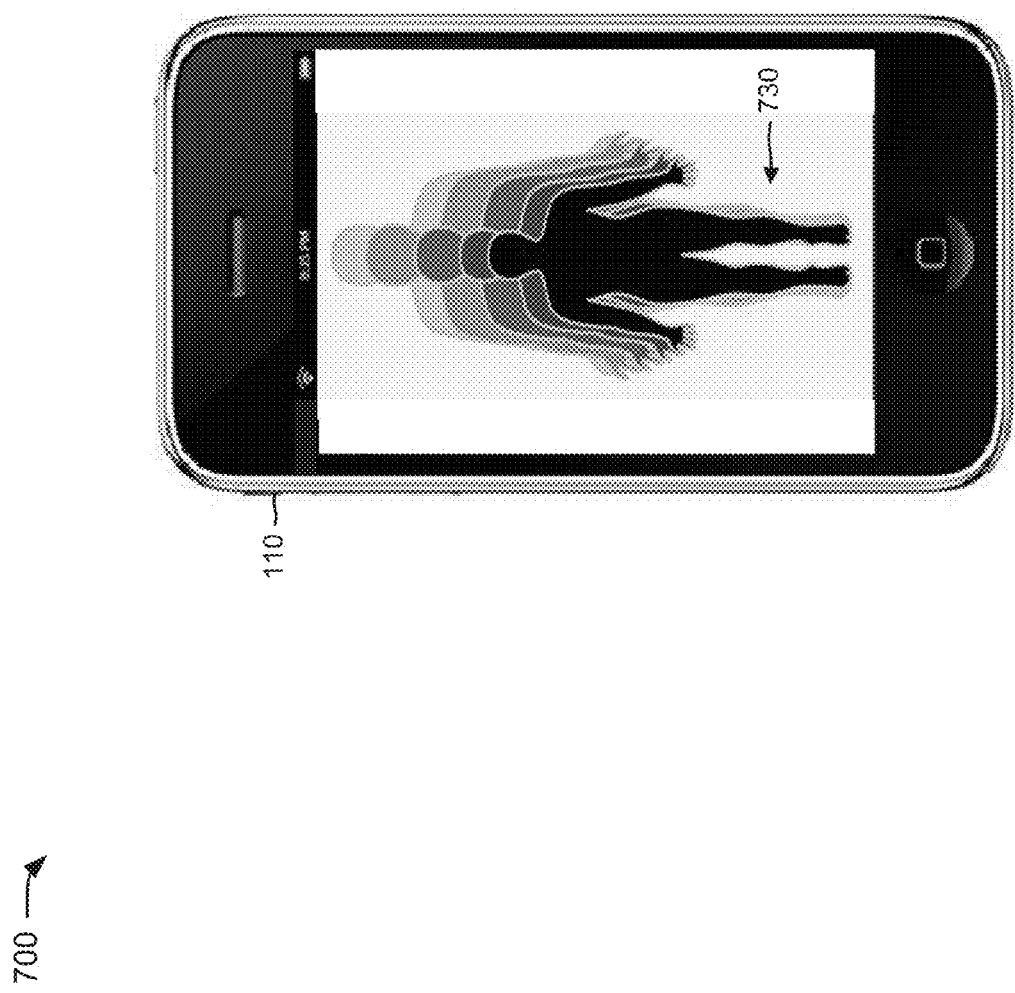

FIGS. 7A-7C are diagrams of example patient motivation user interfaces 700 that may be generated or provided by user device 110. As shown in FIG. 7A, user device 110 may display a graph 710 showing a weight change of a user over a time period (e.g., one year). Graph 710 may enable the user to determine whether to eat healthier foods, exercise more, etc. if the user's weight is greater than a normal weight range. As shown in FIG. 7B, user device 110 may display a graph 720 showing a height change of a user (e.g., a child) over a time period (e.g., multiple years). Graph 720 may enable the child to see how much he or she has grown from the age of five to the age of ten. As shown in FIG. 7C, user device 110 may display an animated FIG. 730 showing body changes of a user over a time period. Animated FIG. 730 may enable the user to determine whether the user has gained or lost weight and/or has grown in height.

FIGS. 8A and 8B are diagrams of example body template user interfaces 800 that may be generated or provided by user device 110. As shown in FIG. 8A, the centric MDR application may enable user device 110 to generate a human interface or body template 810 for a user. Body template 810 may include one or more graphical images of different layers 820 of the user's body. For example, layers 820 may include a normal or skin view layer, a layer that displays all layers provided below the skin view layer, a skeletal layer, a digestive layer, a muscular layer, a lymphatic layer, an endocrine layer, a nervous layer, a cardiovascular layer, a urinary layer, a reproductive layer, and/or one or more other layers (e.g., face, eyes, nose, ears, etc.). Body template 810 may include a two-dimensional or three-dimensional representation of the user's body. As shown in FIG. 8B, the centric MDR application may enable a user, via a user device 110, to flip through layers 820 of body template 810, as indicated by reference number 830. For example, the user may provide a sliding finger gesture to display 210 of user device 110 in order to flip through layers 820 of body template 810. Alternatively, or additionally, the centric MDR application may enable the user to flip through layers 820 using another mechanism, such as a drop-down menu, different finger gestures, voice commands, etc.

Figure 9A:
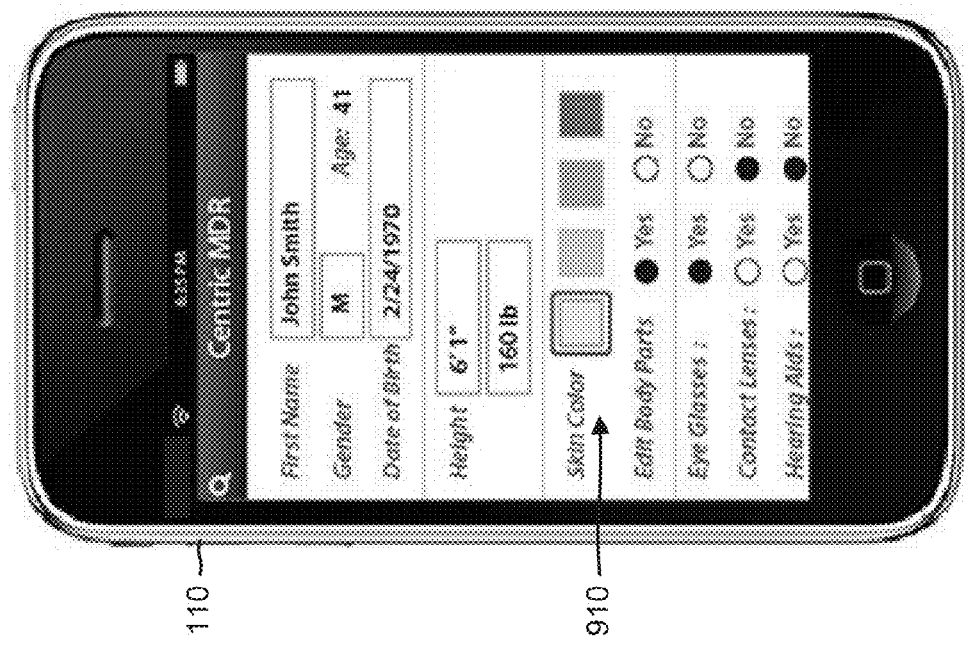
FIGS. 9A-9C are diagrams of example user interfaces, for creating a body template, which may be generated or provided by the user device.
Figure 9B:
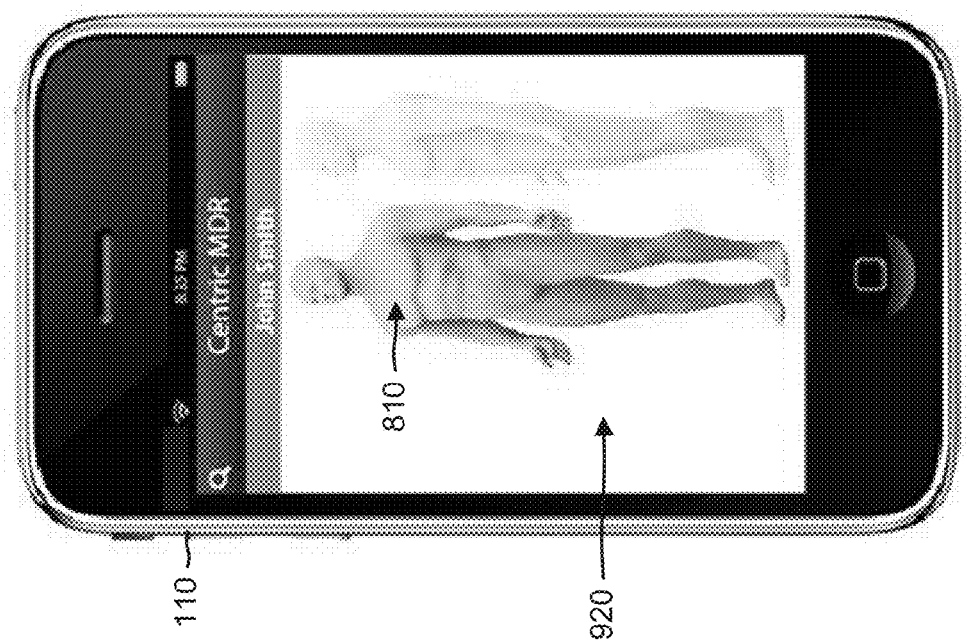
Figure 9C:
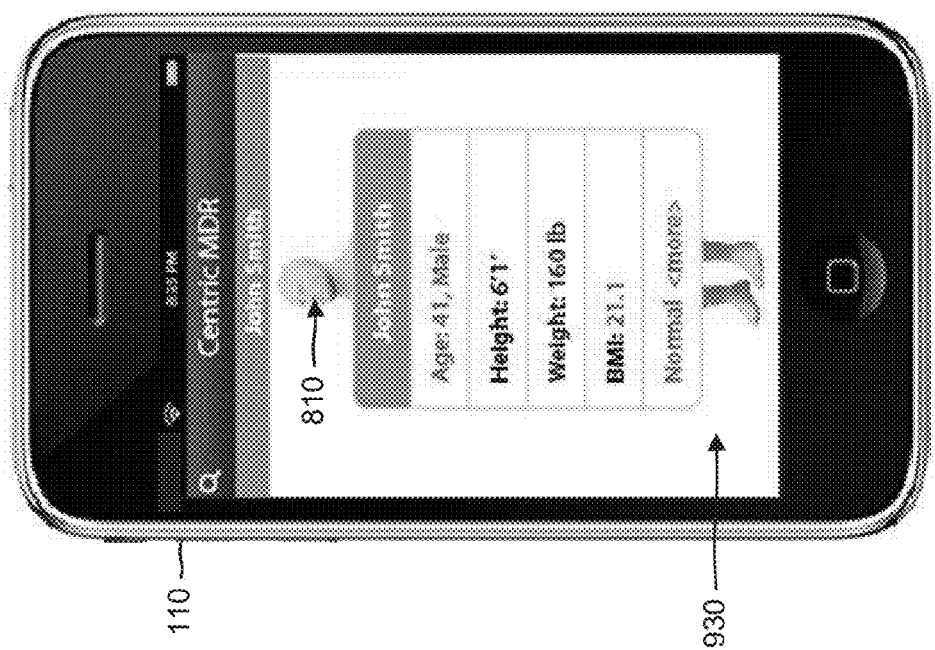

FIGS. 9A-9C are diagrams of example user interfaces 900, for creating body template 810, which may be generated or provided by user device 110. As shown in FIG. 9A, the centric MDR application may enable a user to provide, to user device 110, information 910 that may be used to create body template 810. Information 910 may include, for example, a name of the user, a gender of the user, an age of the user, a height of the user, a weight of the user, a skin color of the user, an option to edit body parts, information about whether the user wears glasses, information about whether the user wears contact lenses, information about whether the user wears a hearing aid, etc. The centric MDR application may utilize information 910 to generate a two-dimensional or a three-dimensional body template 810, as indicated by reference number 920 in FIG. 9B. As shown in FIG. 9C, the user may edit information 910 at any time, and the centric MDR application may utilize the edited information 910 to modify body template 810, as indicated by reference number 930 in FIG. 9C. For example, body template 810 may grow in size as the user gains weight or grows taller.

Figure 10A:
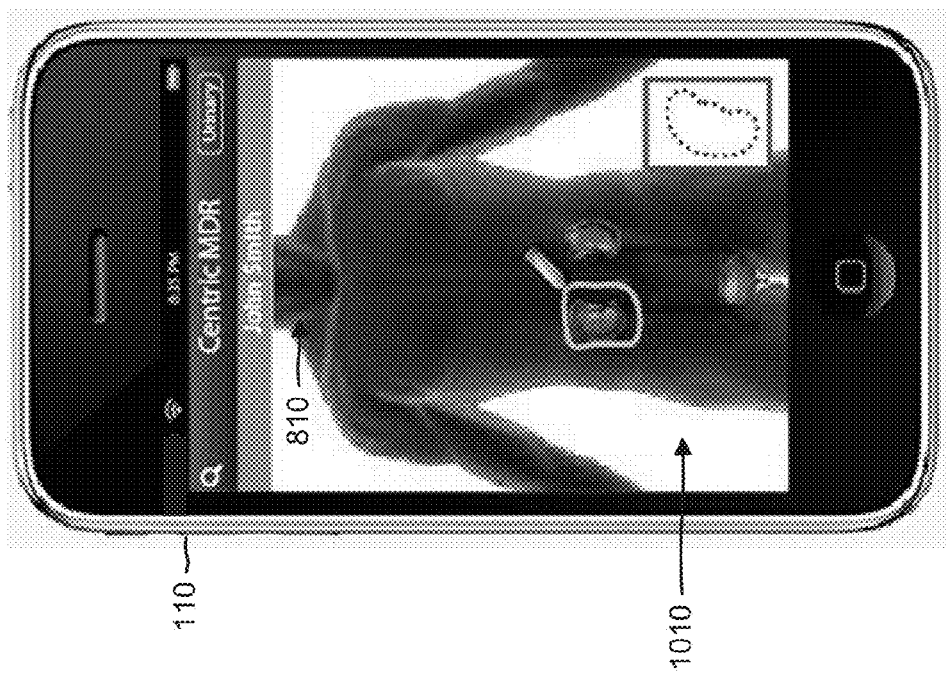
FIGS. 10A and 10B are diagrams of example user interfaces, for editing a body template, which may be generated or provided by the user device.
Figure 10B:
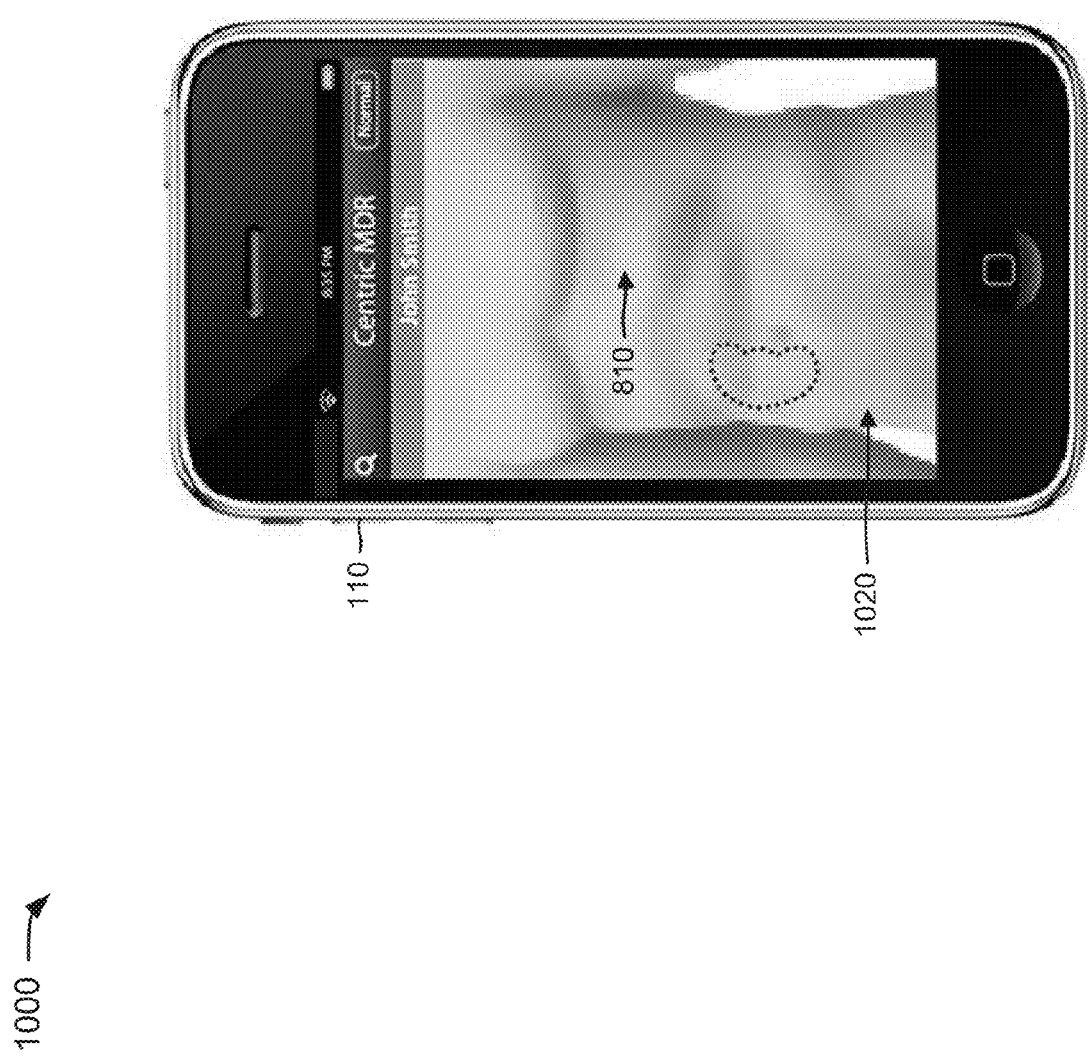

The centric MDR application may enable the user to edit body template 810 at any time. FIGS. 10A and 10B are diagrams of example user interfaces 1000, for editing body template 810, which may be generated or provided by user device 110. As shown in FIG. 10A, the centric MDR application may enable the user to specify missing body parts, such as a missing limb or a missing organ, as indicated by reference number 1010. For example, the user may use finger gestures to select an organ (e.g., a kidney) and may specify that the selected organ is missing. As shown in FIG. 10B, the centric MDR application may highlight the missing organ in body template 810, as indicated by reference number 1020.

Providing accurate information (e.g., via body template 810) to a medical provider may be important for avoiding confusion. For example, assume that a patient is missing a lung and that body template 810 is not updated to reflect the missing lung. If the patient goes for an X-ray without telling the X-ray technician about the missing lung, the technician may be surprised by the X-ray and may contact the patient in a panic. Furthermore, a doctor may not be able to remember a patient's particular body specifications or even the patient's name. For such a doctor, body template 810 may be helpful in refreshing the doctor's memory about the particulars of the patient.

Figure 11B:
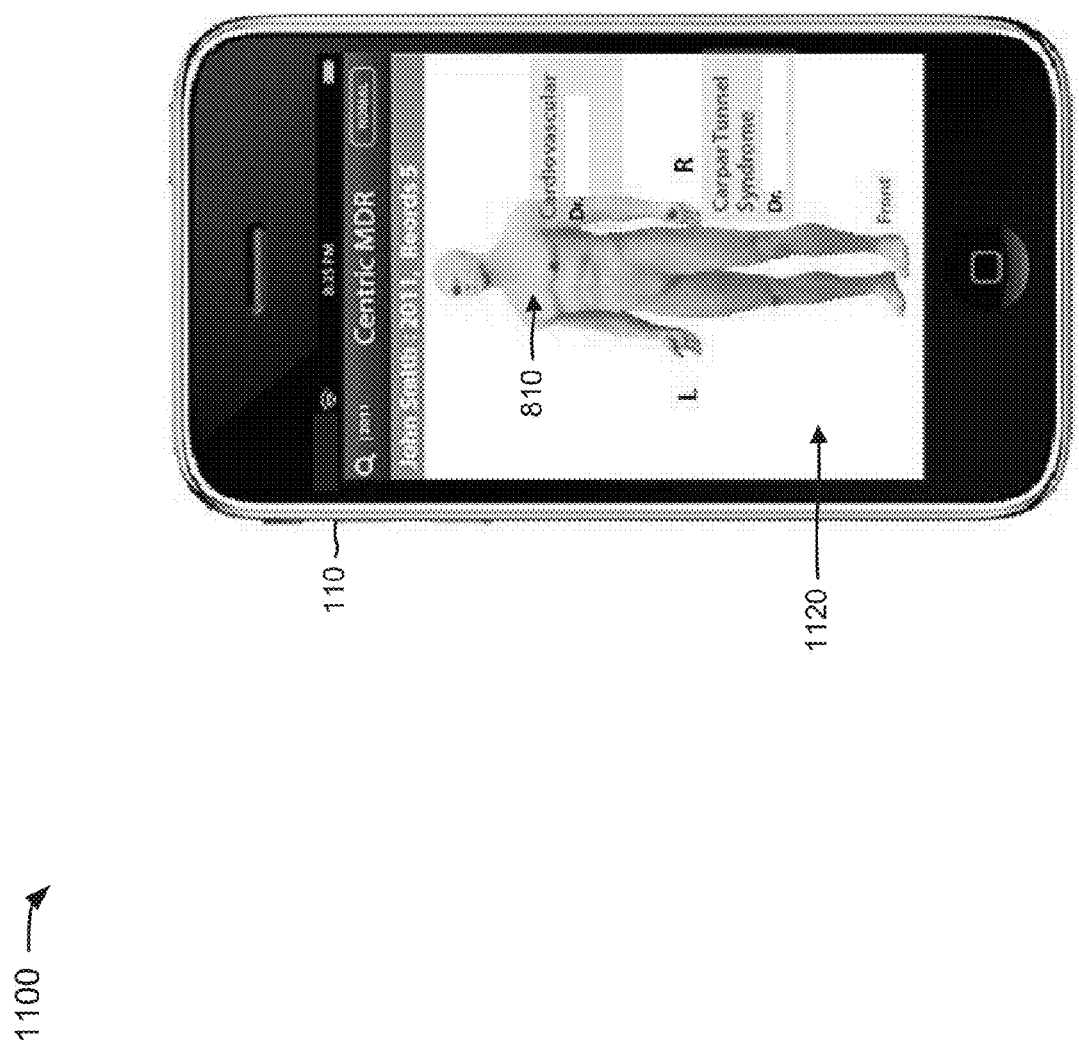

FIGS. 11A and 11B are diagrams of example user interfaces 1100, for reviewing medical records, which may be generated or provided by user device 110. As shown in FIG. 11A, the centric MDR application may enable user device 110 to display body template 810 with one or more information locations, as indicated by reference number 1110. In one example, the information locations may be displayed as markers (e.g., dots) on body template 810. The information locations may be associated with medical data relevant to the locations of information locations on body template 810. For example, as indicated in FIG. 11B by reference number 1120, an information location provided at the chest of body template 810, when selected by a user of user device 110, may display a cardiovascular condition that was diagnosed by Dr. X on Jan. 21, 2011. Another information location provided at the right wrist of body template 810, when selected by a user of user device 110, may display carpal tunnel syndrome that was diagnosed by Dr. Y on Mar. 25, 2011.

Figure 12A:
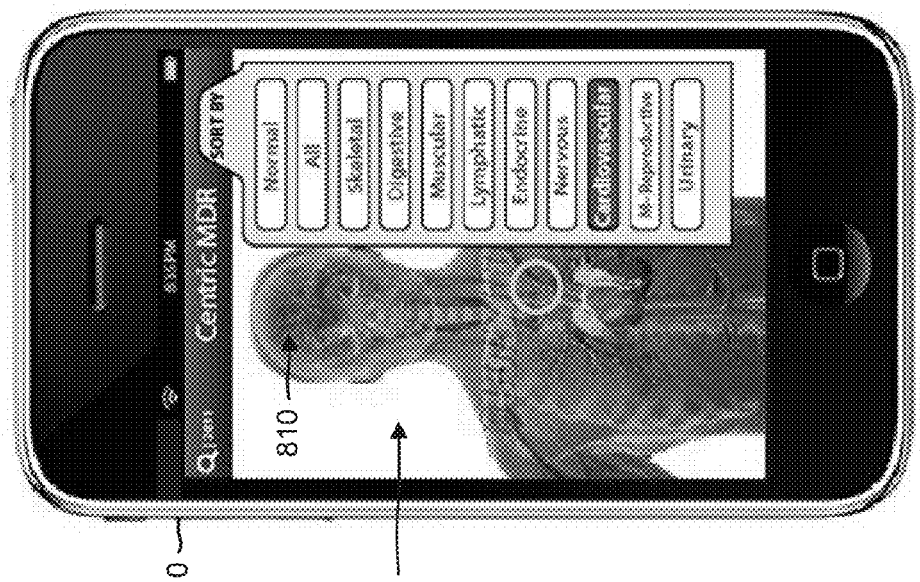
FIGS. 12A and 12B are diagrams of further example user interfaces, for reviewing medical records, which may be generated or provided by the user device.
Figure 12B:
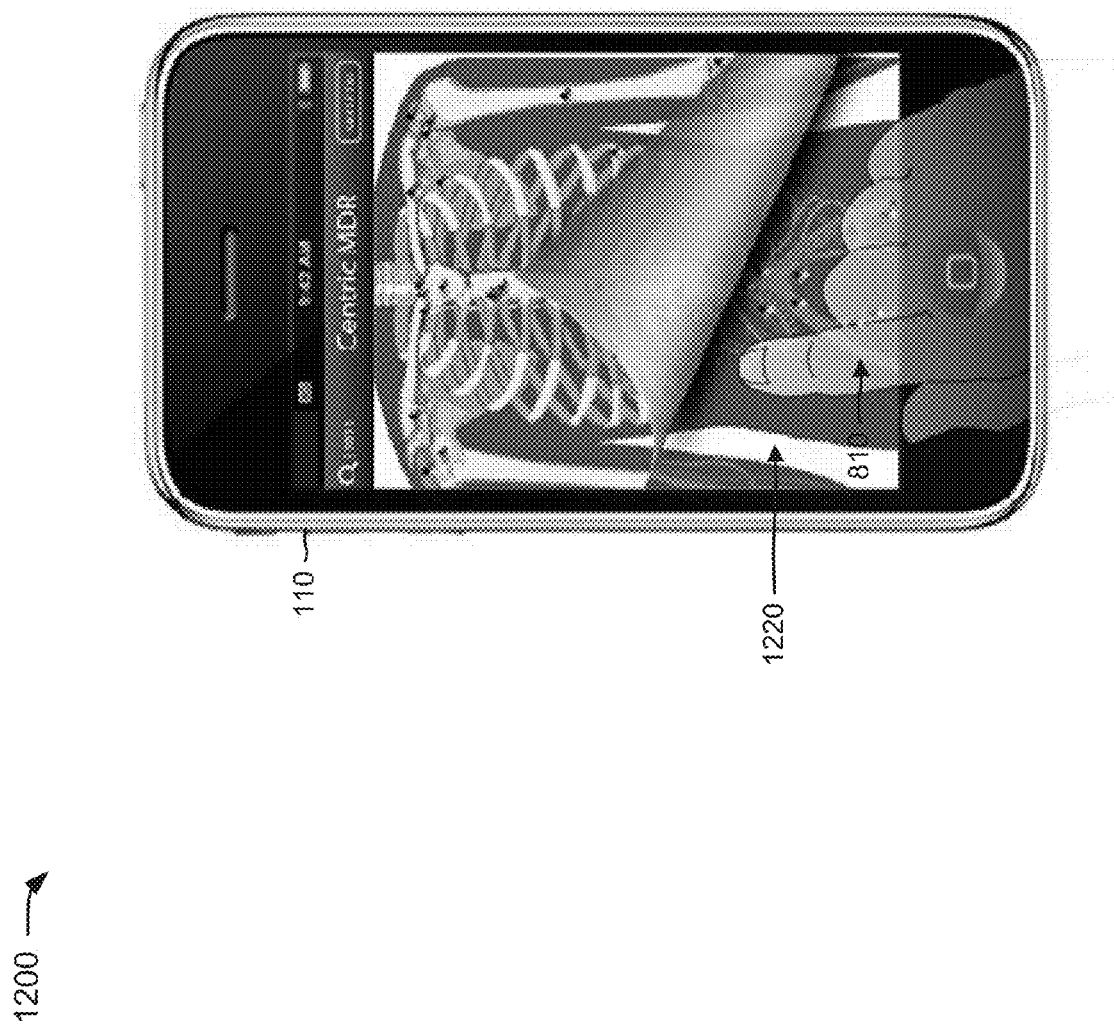

FIGS. 12A and 12B are diagrams of further example user interfaces 1200, for reviewing medical records, which may be generated or provided by user device 110. As shown in FIG. 12A, the centric MDR application may enable the user of user device 110 to review medical records of the user by selecting one or more layers of body template 810, as indicated by reference number 1210. For example, the user may select a cardiovascular layer of body template 810 (e.g., via a drop-down menu), and the centric MDR application may display medical records associated with the user's cardiovascular system (e.g., via one or more information locations, as described above in connection with FIGS. 11A and 11B). Alternatively, or additionally, the centric MDR application may enable the user of user device 110 to review medical records of the user by using finger gestures to select one or more layers of body template 810, as indicated by reference number 1220 in FIG. 12B. For example, the user may use a sliding finger gesture to move from the skeletal layer of body template 810 to a circulatory layer of body template 810. Once the circulatory layer of body template 810 is displayed, the centric MDR application may display medical records associated with the user's circulatory system (e.g., via one or more information locations, as described above in connection with FIGS. 11A and 11B).

The layering system of the centric MDR application may educate the user about the human body and may provide the user with graphical representations of his or her medical issues without having to refer to medical books or medical websites. However, if the user finds the layering system to be too complex, the centric MDR application may enable the user to view the user's medical data at the top (skin level) layer of body template 810, without having to use the layering system.

Figure 13A:
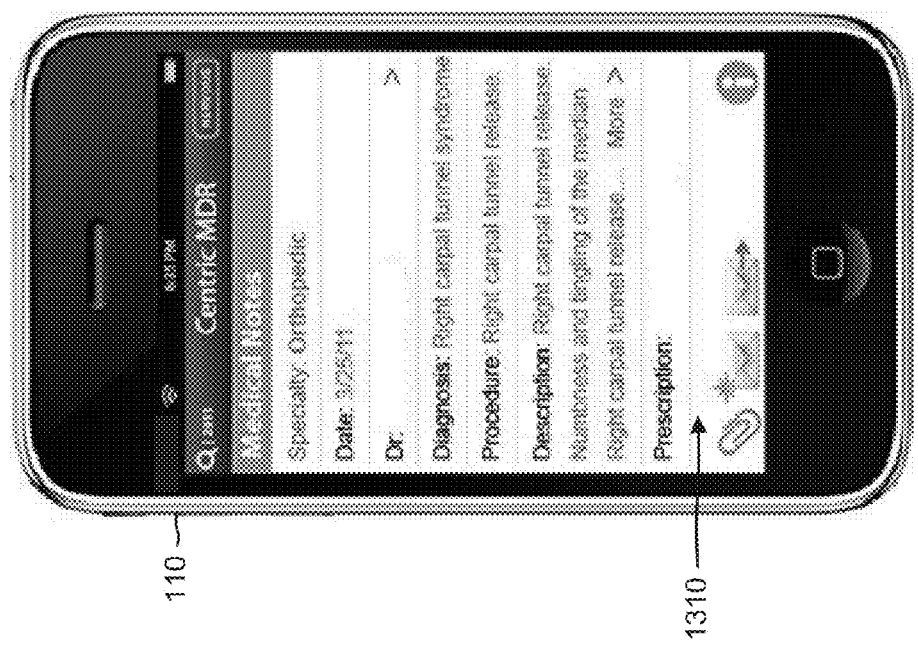
FIGS. 13A and 13B are diagrams of still further example user interfaces, for reviewing medical records, which may be generated or provided by the user device.
Figure 13B:
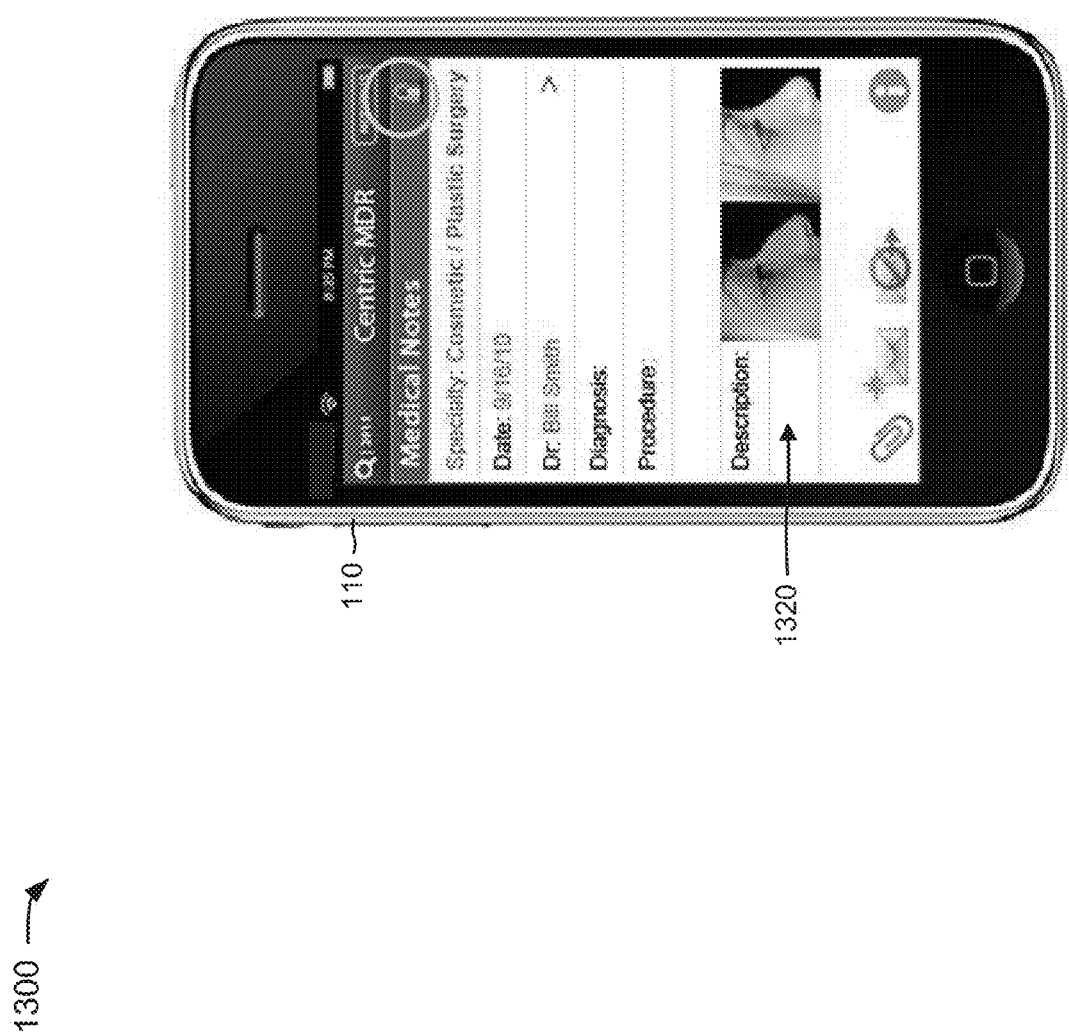

FIGS. 13A and 13B are diagrams of still further example user interfaces 1300, for reviewing medical records, which may be generated or provided by user device 110. As shown in FIG. 13A, the centric MDR application may enable the user of user device 110 to review medical records, such as medical notes, as indicated by reference number 1310. For example, the medical notes may indicate that the user saw an orthopedic doctor (Dr. Y) on Mar. 25, 2011, that the doctor diagnosed right carpal tunnel syndrome for the user, and that the doctor prescribed a drug for the condition. In one example implementation, the medical records may be unsecure medical records that may be transferred (e.g., via email or a Bluetooth wireless exchange) to a doctor's user device 110 by selecting one of the icons provided at the bottom of user interface 1300. Furthermore, the user may select one of the pieces of information provided by the medical notes in order to see additional information. For example, if the user selects Dr. Y, the centric MDR application may display a telephone number, a mailing address, an email address, etc. associated with Dr. Y. If the user selects the prescription for a drug, the centric MDR application may display side effects, recommended dosages, product warnings, etc. associated with a drug.

As shown in FIG. 13B by reference number 1320, the medical records (e.g., medical notes) may be secure medical records, as indicated by the padlock at the top of user interface 1300 in FIG. 13B. The user may transfer the secure medical records to a doctor's user device 110 only after the secure medical records are unlocked by the user. After the user unlocks the secure medical records, the user may transfer the secure medical records to the doctor's user device 110 by selecting one of the icons provided at the bottom of user interface 1300.

Figure 14A:
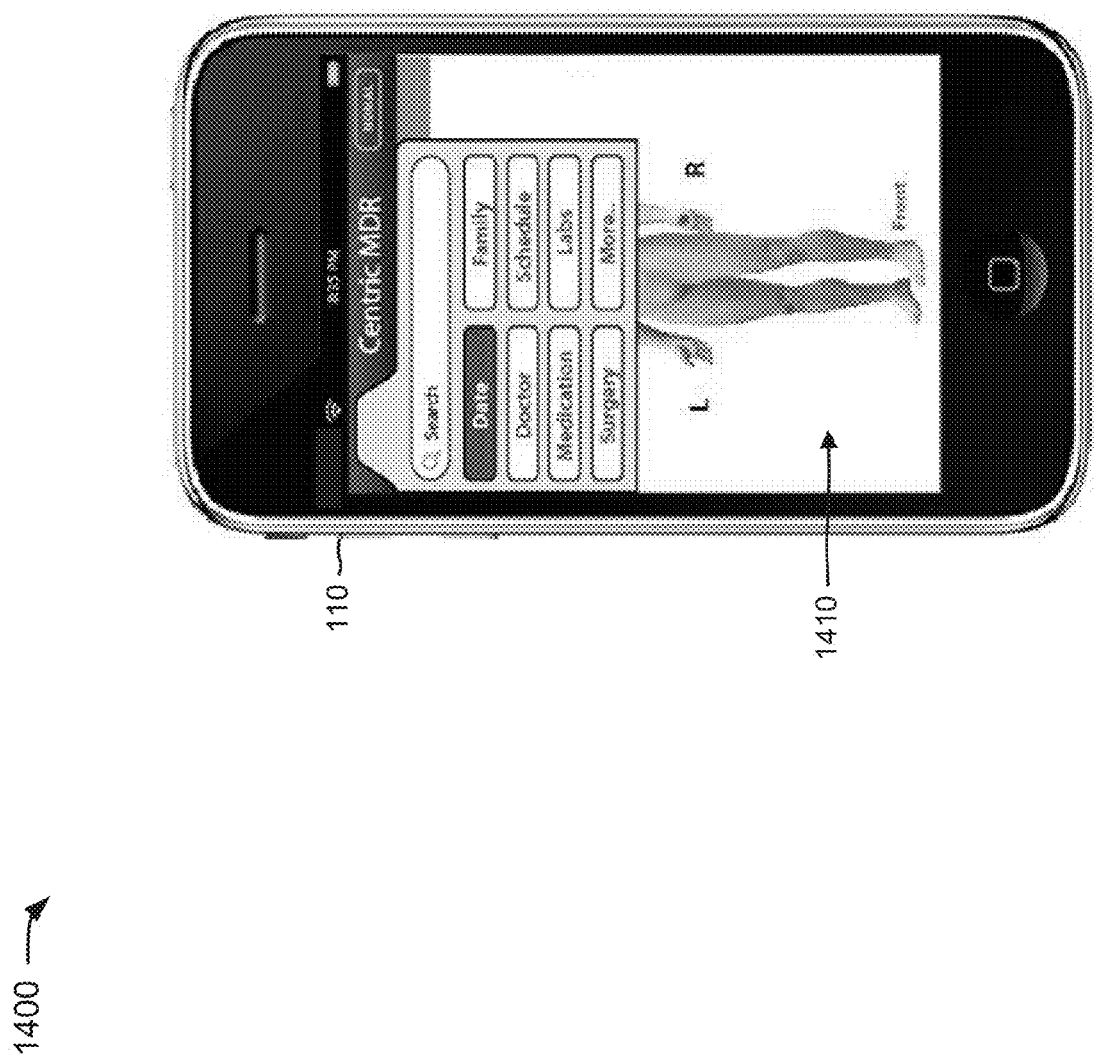
FIGS. 14A-14C are diagrams of example user interfaces, for searching for medical records, which may be generated or provided by the user device.
Figure 14B:
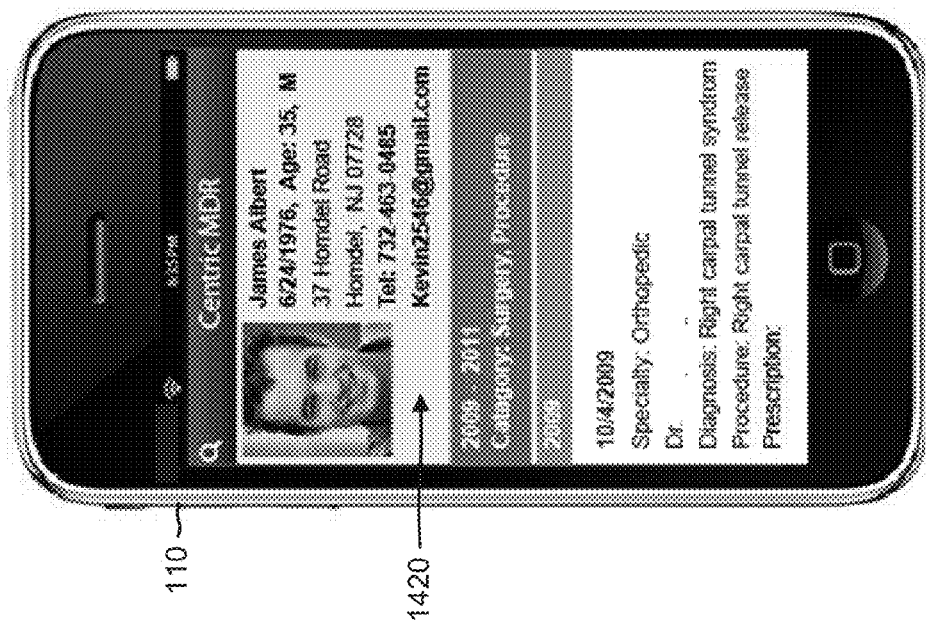
Figure 14C:
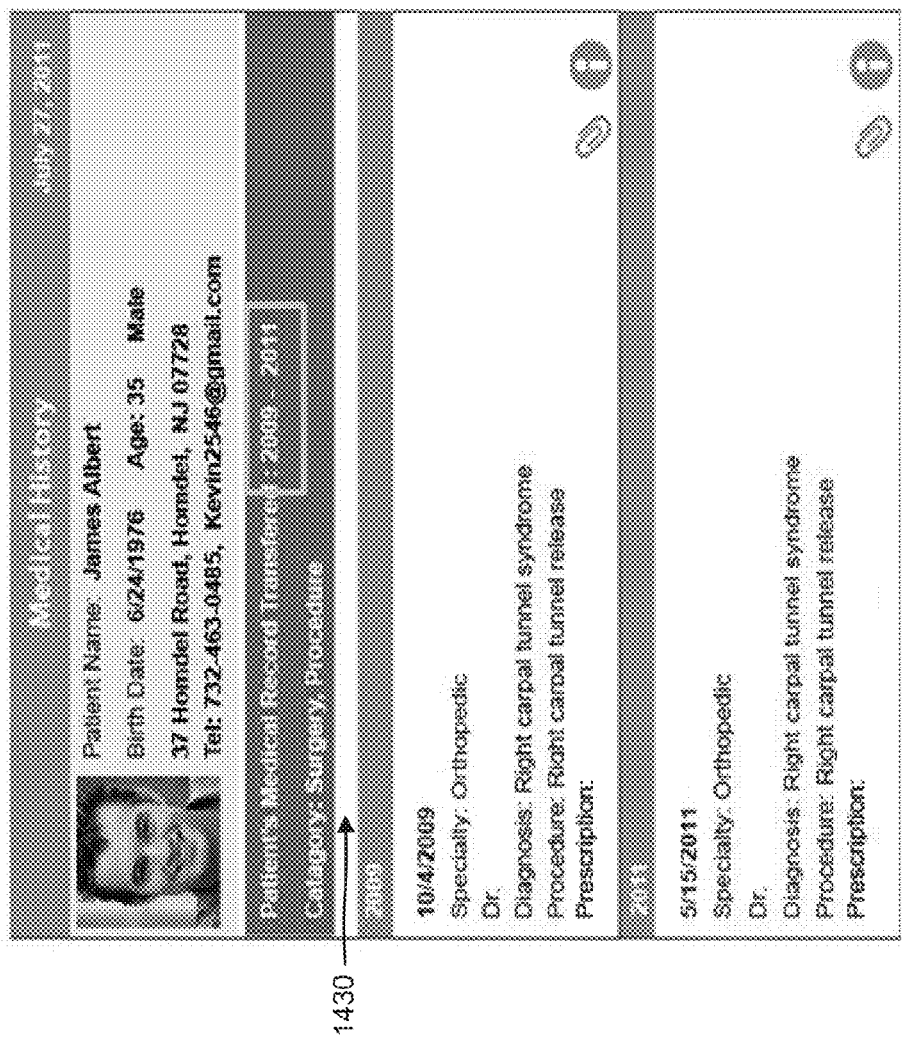

FIGS. 14A-14C are diagrams of example user interfaces 1400, for searching for medical records, which may be generated or provided by user device 110. As shown in FIG. 14A, the centric MDR application may enable the user of user device 110 to search for medical records, as indicated by reference number 1410. For example, the user may search for medical records based on a date, a doctor, a medication, surgery information, a family member, a schedule, lab information, medical provider information, test results, etc. User device 110, via the centric MDR application, may receive a search request for a medical record, and may search for the medical record based on the search request. In one example, user device 110 may search for the medical record in memory 310 of user device 110.

Once the medical record is located, user device 110 may display the medical record to the user, as indicated by reference number 1420 in FIG. 14B. Medical record 1420 may include, for example, user information (e.g., a name, an address, a date of birth, an age, a sex, a telephone number, an email address, etc.); surgical procedure information; medical notes; a photograph of the user (e.g., obtained from a phone contact list); etc. The centric MDR application may enable user device 110 to share one or more medical records with a doctor's user device 110, and the doctor's user device 110 may display a medical record, as indicated by reference number 1430 in FIG. 14C. In one example, medical record 1430 may include medical information for the user of user device 110 for a particular time period (e.g., the years 2009 to 2011). Medical record 1430 may include the same or similar information as provided for medical record 1420.

Although the user interfaces of FIGS. 5A-14C depict a variety of information, in other implementations, the user interfaces may depict less information, different information, differently arranged information, or additional information than depicted in FIGS. 5A-14C. In one example implementation, microphone 230 (FIG. 2) may be utilized by the user of user device 110 to provide voice commands to the centric MDR application. The voice commands may be used in place of and/or in addition to the finger gestures and inputs described above in connection with FIGS. 5A-14C.

Figure 16:
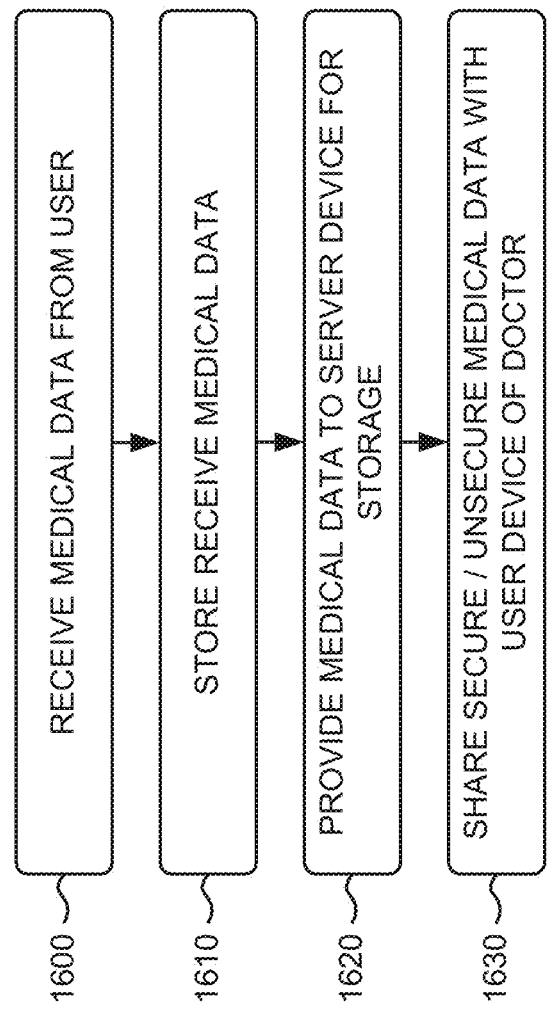

FIGS. 15 and 16 are flow charts of an example process 1500 for providing layered body template-based medical records according to an implementation described herein. In one implementation, process 1500 may be performed by user device 110. Alternatively, or additionally, some or all of process 1500 may be performed by another device or group of devices, including or excluding user device 110.

As shown in FIG. 15, process 1500 may include creating a body template based on medical data received from a user (block 1510), and editing the body template based on changes to the medical data provided by the user (block 1520). For example, in an implementation described above in connection with FIGS. 9A-9C, the centric MDR application may enable a user to provide, to user device 110, information 910 that may be used to create body template 810. Information 910 may include, for example, a name of the user, a gender of the user, an age of the user, a height of the user, a weight of the user, a skin color of the user, an option to edit body parts, information about whether the user wears glasses, information about whether the user wears contact lenses, information about whether the user wears a hearing aid, etc. The centric MDR application may utilize information 910 to generate a two-dimensional or a three-dimensional body template 810, as indicated by reference number 920. The user may edit information 910 at any time, and the centric MDR application may utilize the edited information 910 to modify body template 810, as indicated by reference number 930.

As further shown in FIG. 15, process 1500 may include displaying the body template, with information locations, to the user (block 1530), and displaying, to the user, information associated with a particular information location when the particular information location is selected by the user (block 1540). For example, in an implementation described above in connection with FIGS. 11A and 11B, the centric MDR application may enable user device 110 to display body template 810 with one or more information locations, as indicated by reference number 1110. In one example, the information locations may be displayed as markers (e.g., dots) on body template 810. The information locations may be associated with medical data relevant to the locations of information locations on body template 810. As indicated by reference number 1120, an information location provided at the chest of body template 810, when selected by a user of user device 110, may display a cardiovascular condition that was diagnosed by Dr. X on Jan. 21, 2011. Another information location provided at the right wrist of body template 810, when selected by a user of user device 110, may display carpal tunnel syndrome that was diagnosed by Dr. Y on Mar. 25, 2011.

Returning to FIG. 15, process 1500 may include displaying layers of the body template for manipulation by the user (block 1550). For example, in an implementation described above in connection with FIGS. 8A and 8B, the centric MDR application may enable user device 110 to generate body template 810 for a user. Body template 810 may include one or more graphical images of different layers 820 of the user's body. For example, layers 820 may include a normal or skin view layer, a layer that displays all layers provided below the skin view layer, a skeletal layer, a digestive layer, a muscular layer, a lymphatic layer, an endocrine layer, a nervous layer, a cardiovascular layer, a urinary layer, a reproductive layer, and other layers (e.g., face, eyes, nose, ears, etc.). The centric MDR application may enable a user, via a user device 110, to flip through layers 820 of body template 810, as indicated by reference number 830. For example, the user may provide a sliding finger gesture to display 210 of user device 110 in order to flip through layers 820 of body template 810. Alternatively, or additionally, the centric MDR application may enable the user to flip through layers 820 using another mechanism, such as a drop-down menu, different finger gestures, voice commands, etc.

As further shown in FIG. 15, process 1500 may include receiving a request for a particular medical record of the medical data (block 1560), searching for the particular medical record based on the request (block 1570), and displaying the particular medical record to the user (block 1580). For example, in an implementation described above in connection with FIGS. 14A and 14B, the centric MDR application may enable the user of user device 110 to search for medical records, as indicated by reference number 1410. For example, the user may search for medical records based on a date, a doctor, a medication, surgery information, a family member, a schedule, lab information, medical provider information, test results, etc. User device 110, via the centric MDR application, may receive a search request for a medical record, and may search for the medical record based on the search request. In one example, user device 110 may search for the medical record in memory 310 of user device 110. Once the medical record is located, user device 110 may display the medical record to the user, as indicated by reference number 1420.

Process block 1510 may include the process blocks depicted in FIG. 16. As shown in FIG. 16, process block 1510 may include receiving the medical data from the user (block 1600), storing the medical data (block 1610), providing the medical data to a server device for storage (block 1620), and sharing secure and/or unsecure medical data with a user device of a doctor (block 1630). For example, in an implementation described above in connection with FIGS. 4, 13A, and 13B, the centric MDR application may include a mobile application that enables a user to input and store patient medical information in user devices 110. For example, the centric MDR application may enable the first user to input and store medical data 410 in user device 110-1 (e.g., in memory 310). The first user may instruct user device 110-1 to provide medical data 410 to server 120. Server 120 may receive medical data 410 and may store medical data 410 in a memory device associated with server 120. The centric MDR application may enable the user of user device 110 to review medical records, such as medical notes, as indicated by reference number 1310. In one example, the medical records may be unsecure medical records that may be transferred to a doctor's user device 110 by selecting one of the icons provided at the bottom of user interface 1300. In another example, the medical records (e.g., medical notes) may be secure medical records, as indicated by the padlock at the top of user interface 1300. The user may transfer the secure medical records to a doctor's user device 110 only after the secure medical records are unlocked by the user. After the user unlocks the secure medical records, the user may transfer the secure medical records to the doctor's user device 110 by selecting one of the icons provided at the bottom of user interface 1300.

Systems and/or methods described herein may provide a centric MDR application for storing patient medical information in a user device (e.g., a mobile computation and/or communication device) associated with the patient. The systems and/or methods may enhance patient health and safety by reducing medical errors due to incorrect or unavailable medical information. The systems and/or methods may educate patients regarding their health, and may provide improved patient and doctor collaboration.

The foregoing description of implementations provides illustration and description, but is not intended to be exhaustive or to limit the implementations to the precise form disclosed. Modifications and variations are possible in light of the above teachings or may be acquired from practice of the implementations.

For example, while series of blocks have been described with regard to FIGS. 15 and 16, the order of the blocks may be modified in other implementations. Further, non-dependent blocks may be performed in parallel.

It will be apparent that example aspects, as described above, may be implemented in many different forms of software, firmware, and hardware in the implementations illustrated in the figures. The actual software code or specialized control hardware used to implement these aspects should not be construed as limiting. Thus, the operation and behavior of the aspects were described without reference to the specific software code—it being understood that software and control hardware could be designed to implement the aspects based on the description herein.

Even though particular combinations of features are recited in the claims and/or disclosed in the specification, these combinations are not intended to limit the disclosure of the invention. In fact, many of these features may be combined in ways not specifically recited in the claims and/or disclosed in the specification. Although each dependent claim listed below may directly depend on only one other claim, the disclosure of the invention includes each dependent claim in combination with every other claim in the claim set.

No element, act, or instruction used in the present application should be construed as critical or essential to the invention unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed is:

1. A method comprising:
generating, by a user device, a graphical user interface for presenting a human body template including a plurality of system-level layers representative of anatomical systems of a user;
obtaining, by the user device, first medical information associated with the user and corresponding to a first bodily location on a first system-level layer;
obtaining, by the user device, second medical information associated with the user and corresponding to a second bodily location on a second system-level layer;
receiving, via the graphical user interface, selection of the first system-level layer for display;
displaying, via a display of the user device and responsive to the selection of the first system-level layer, the first system-level layer including a first visual indicator corresponding to the first bodily location;
receiving, via the graphical user interface, selection of the first visual indicator;
presenting, via the graphical user interface and responsive to the selection of the first visual indicator, the first medical information; and
presenting, via the graphical user interface, superimposed representative bodily images corresponding to changes in a physical stature of the user as a function of time.

2. The method of claim 1, further comprising:
displaying, responsive to receiving a request for a medical record of the presented first medical information, at least a portion of the medical record via the graphical user interface, the medical record identifying a diagnosed medical condition of the user and including an indication whether the medical record is secured and nontransferable or unsecured and transferable.

3. The method of claim 1, further comprising:
presenting, via the graphical user interface and responsive to receiving a request for one or more medical records of the presented first medical information, a drop-down menu including selectable search criteria corresponding to the one or more medical records, the one or more medical records identifying at least one diagnosed medical condition of the user.

4. The method of claim 1, further comprising:
receiving, via the graphical user interface, selection of the second system-level layer for display after the selection of the first system-level layer for display;
removing, responsive to the selection of the second system-level layer, the first system-level layer from the display; and displaying the second system-level layer, including a second visual indicator corresponding to the second location, via the display without display of the second medical information.

5. The method of claim 4, further comprising:
receiving, via the graphical user interface, selection of the second visual indicator; and
presenting, via the graphical user interface and responsive to the selection of the second visual indicator, the second medical information with the second visual indicator.

6. The method of claim 1, wherein generating the graphical user interface for presenting the human body template including the plurality of system-level layers representative of anatomical systems of the user, comprises generating the plurality of system-level layers to include a top layer, the method further comprising:
displaying, via the display and responsive to the selection of the top layer, the top layer including the first visual indicator corresponding to the first bodily location and a second visual indicator corresponding to the second location.

7. The method of claim 6, wherein generating the plurality of system-level layers to include a top layer comprises generating the top layer to be representative of a skin layer.

8. A device comprising:
a display;
a memory to store instructions; and
a processor to execute the instructions to:
generate a graphical user interface for presenting a human body template including a plurality of system-level layers representative of anatomical systems of a user,
obtain first medical information, associated with the user, corresponding to a first bodily location on a first system-level layer,
obtain second medical information, associated with the user, corresponding to a second location on a second system-level layer,
receive, via the graphical user interface, selection of the first system-level layer for display,
display, via the display and responsive to the selection of the first system-level layer, the first system-level layer including a first visual indicator corresponding to the first bodily location,
receive, via the graphical user interface, selection of the first visual indicator, present, via the graphical user interface and responsive to the selection of the first visual indicator, the first medical information, and
present, via the graphical user interface, superimposed representative bodily images corresponding to changes in a physical stature of the user as a function of time.

9. The device of claim 8, wherein the processor is to execute the instructions to display, responsive to receiving a request for a medical record of the presented first medical information, at least a portion of the medical record via the graphical user interface, the medical record identifying a diagnosed medical condition of the user and including an indication whether the medical record is secured and non-transferable or unsecured and transferable.

10. The device of claim 9, wherein the processor is to execute the instructions to present, via the graphical user interface and responsive to receiving a request for one or more medical records of the presented first medical information, a drop-down menu including selectable search criteria corresponding to the one or more medical records, the one or more medical records identifying at least one diagnosed medical condition of the user.

11. The device of claim 8, wherein the processor is to further execute the instructions to:
receive, via the graphical user interface, selection of the second system-level layer for display after the selection of the first system-level layer for display;
remove, responsive to the selection of the second system-level layer, the first system-level layer from the display; and
display the second system-level layer, including a second visual indicator corresponding to the second location, via the display without display of the second medical information.

12. The device of claim 11, wherein the processor is to further execute the instructions to:
receive, via the graphical user interface, selection of the second visual indicator; and
present, via the graphical user interface and responsive to the selection of the second visual indicator, the second medical information with the second visual indicator.

13. The device of claim 8, wherein, when generating a graphical user interface for presenting a human body template including a plurality of system-level layers representative of anatomical systems of a user, the processor is to further execute the instructions to:
generate the plurality of system-level layers to include a top layer, and
display via the display and responsive to the selection of the top layer, the top layer including the first visual indicator corresponding to the first bodily location and a second visual indicator corresponding to the second location.

14. The device of claim 13, wherein, when generating the plurality of system-level layers to include a top layer, the processor is to execute the instructions further to generate the top layer to be representative of a skin layer.

15. A non-transitory computer-readable medium, comprising instructions that, when executed by a processor of a device, cause the processor to:
generate a graphical user interface of a user device for presenting a human body template including a plurality of system-level layers representative of anatomical systems of a user;
obtain first medical information, associated with the user, corresponding to a first bodily location on a first system-level layer;
obtain second medical information, associated with the user, corresponding to a second location on a second system-level layer;
receive, via the graphical user interface, selection of the first system-level layer for display;
display, via a display of the user device and responsive to the selection of the first system-level layer, the first system-level layer including a first visual indicator corresponding to the first bodily location;
receive, via the graphical user interface, selection of the first visual indicator;
present, via the graphical user interface and responsive to the selection of the first visual indicator, the first medical information, and
present, via the graphical user interface, superimposed representative bodily images corresponding to changes in a physical stature of the user as a function of time.

16. The non-transitory computer-readable medium of claim 15, wherein the instructions cause the processor to display, responsive to receiving a request for a medical record of the presented first medical information, at least a portion of the medical record via the graphical user interface, the medical record identifying a diagnosed medical condition of the user and including whether the medical record is secured and nontransferable or unsecured and transferable.

17. The non-transitory computer-readable medium of claim 16, wherein the instructions cause the processor to present, via the graphical user interface and responsive to receiving a request for one or more medical records of the presented first medical information, a drop-down menu including selectable search criteria corresponding to the one or more medical records, the one or more medical records identifying at least one diagnosed medical condition of the user.

18. The non-transitory computer-readable medium of claim 15, wherein the instructions further cause the processor to:
- receive, via the graphical user interface, selection of the second system-level layer for display after the selection of the first system-level layer for display;
- remove, responsive to the selection of the second system-level layer, the first system-level layer from the display; and
- display the second system-level layer, including a second visual indicator corresponding to the second location, via the display without display of the second medical information.

19. The non-transitory computer-readable medium of claim 18, wherein the instructions further cause the processor to:
- receive, via the graphical user interface, selection of the second visual indicator; and
- present, via the graphical user interface and responsive to the selection of the second visual indicator, the second medical information with the second visual indicator.

20. The non-transitory computer-readable medium of claim 15, wherein, when generating the graphical user interface for presenting the human body template including the plurality of system-level layers representative of anatomical systems of the user, the instructions further cause the processor to:
- generate the plurality of system-level layers to include a top layer, and
- display via the display and responsive to the selection of the top layer, the top layer including the first visual indicator corresponding to the first bodily location and a second visual indicator corresponding to the second location.

* * * * *